US006133232A

United States Patent [19]
De Robertis et al.

[11] Patent Number: 6,133,232
[45] Date of Patent: *Oct. 17, 2000

[54] ENDODERM, CARDIAC AND NEURAL INDUCING FACTORS

[75] Inventors: Edward M. De Robertis, Pacific Palisades, Calif.; Tewis Bouwmeester, Heidelberg, Germany

[73] Assignee: The Regents of the University of California, Oakland, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/878,474

[22] Filed: Jun. 18, 1997

Related U.S. Application Data

[60] Provisional application No. 60/020,150, Jun. 20, 1996.

[51] Int. Cl.$^7$ .............................. A61K 38/18; C07K 14/46
[52] U.S. Cl. .......................... 514/12; 424/198.1; 530/350
[58] Field of Search ........................... 514/12; 424/198.1; 530/350

[56] References Cited

U.S. PATENT DOCUMENTS 5,457,048   10/1995   Pasquale et al. ...................... 435/252.3

FOREIGN PATENT DOCUMENTS

94/05791   3/1994   WIPO .
94/05800   3/1994   WIPO .

OTHER PUBLICATIONS

Ham et al. Media and growth requirements. Methods Enzymology, (Mar. 1979), vol. 58, pp. 44–93.
Bouwmeester et al., "Cerberus is a head–inducing secreted factor expressed in the anterior endoderm of Spemann's organizer," *Nature*, 382:6592, pp. 595–601 (Aug. 15, 1996).
Christian et al., "Interactions between Xwnt–8 and Spemann organizer signaling pathways generate dorsoventral pattern in the embryonic mesoderm of Xenopus," *Genes & Development*, pp. 13–28 (1993).
Gribskov et al, "[9] Profile Analysis," *Methods of Enzymology*, 183, pp. 146–159 (1990).
Krasnow et al., "dishevelled is a component of the frizzled signaling pathway in Drosophila," *Development*, 121, pp. 4095–4102 (1995).
Leyns et al., "Frzb–1 Is a Secreted Antagonist of Wnt Signaling Expressed in the Spemann Organizer," *Cell*, 88, pp. 747–756 (Mar. 21, 1997).
Mayr et al., "Fritz: a secreted frizzled–related protein that inhibits Wnt activity," *Mechanisms of Development*, 63, pp. 109–125 (1997).
Moon et al., "Structural Related Receptors and Antagonists Compete for Secreted Wnt Ligands," *Cell*, 88, pp. 725–728 (Mar. 21, 1997).
Sano et al., "Protocadherins: a large family of cadherin–related molecules in central nervous system," *The EMBO Journal*, 12:6, pp. 2249–2256 (1993).
Sasai et al., "Xenopus chordin: A Novel Dorsalizing Factor Activated by Organizer–Specific Homeobox Genes," *Cell*, 79, pp. 779–790 (Dec. 2, 1994).
Sasai et al., "Regulation of neural induction by the Chd and Bmp–4 antagonistic patterning signals in Xenopus," *Nature*, 376, pp. 333–336 (Jul. 27, 1995).
Sokol et al., A Mouse Macrophage Factor induces Head Structures and Organizes a Body Axis in Xenopus, *Science*, 249, pp. 561–564 (Aug. 3, 1990).
Smith et al., "Injection Xwnt–8 RNA Acts Early in Xenopus Embryos to Promote Formation of a Vegetal Dorsalizing Center," *Cell* 67, pp. 753–765 (Nov. 15, 1991).
Smith et al., "Expression Cloning of noggin, A new Dorsalizing Factor Localized to the Spemann Organizer in Xenopus Embryos," *Cell*, 70 , pp. 829–840 (Sep. 4, 1992).
Vinson et al., "A Drosophilia tissue polarity locus encodes a protein containing seven potential transmembrane domains," *Nature*, 338, pp. 263–264 (Mar. 16, 1989).
Vinson et al., "Directional non–cell autonomy and the transmission of polarity information by the frizzled gene of Drospohila," *Nature*, 329 pp. 549–551 (Oct. 8, 1987).
Wang et al., "A Large Family of Putative Transmembrane Receptors Homologous to the Product of the Drosophilia Tissue Polarity Gene frizzled," *J. of Biol. Chem.*, 271:8, pp. 4468–4476 (Feb.23, 1996).
Wang et al. "Frzb, a Secreted Protein Expressed in the Spemann Organizer, Binds and Inhibits Wnt–8," *Cell*, 88, pp. 757–766 (Mar. 21, 1997).
Nathan C; Sporn M. Cytokines in context. J. Cell Biol., (Jun. 1991) 113 (5) 981–986.
Marieb E N. In, Human Anatomy and Physiology, Second Edition. 1992. The Benjamin/Cummings Publishing Co., Inc. pp. 373–375.
Daniel et al. Virology, (Aug. 1, 1994) 202 (2) 540–549.

*Primary Examiner*—David Romeo
*Assistant Examiner*—Elizabeth Kemmerer
*Attorney, Agent, or Firm*—Majestic, Parsons, Siebert & Hsue P.C.

[57] ABSTRACT

Two novel proteins have been designated "cerberus" and "frzb-1," respectively. Cerberus is expressed as a secreted peptide during embryogenesis of the Xenopus embryo, and is expressed specifically in the head organizer region. This new molecule has endodermal, cardiac, and neural tissue inducing activity, that should prove useful in therapeutic, diagnostic, and clinical applications requiring regeneration, differentiation, or repair of these and other tissues. Frzb-1 is a soluble antagonist of growth factors of the Wnt family that acts by binding to Wnt growth factors in the extracellular space. A third novel protein is designated "PAPC" which promotes the formation of dorsal mesoderm and somites in the embryo.

10 Claims, 18 Drawing Sheets

```
MLLNVLRICI  IVCLVNDGAG  KHSEGRERTK  TYSLNSRGYF   40
RKERGARRSK  ILLVNTKGLD  EPHIGHGDFG  LVAELFDSTR   80
THTNRKEPDM  NKVKLFSTVA  HGNKSARRKA  YNGSRRNIFS  120
RRSFDKRNTE  VTEKPGAKMF  WNNFLVKMNG  APQNTSHGSK  160
AQEIMKEACK  TLPFTQNIVH  ENCDRMVIQN  NLCFGKCISL  200
HVPNQQDRRN  TCSHCLPSKF  TLNHLTLNCT  GSKNVVKVVM  240
MVEECTCEAH  KSNFHQTAQF  NMDTSTTLHH              270
```

Figure 1

```
GAATTCCCAG CAAGTCGCTC AGAAACACTG CAGGGTCTAG ATATCATACA ATGTTACTAA    60
CTTAAGGGTC GTTCAGCGAG TCTTTGTGAC GTCCCAGATC TATAGTATGT TACAATGATT

ATGTACTCAG GATCTGTATT ATCGTCTGCC TTGTGAATGA TGGAGCAGGA AAACACTCAG   120
TACATGAGTC CTAGACATAA TAGCAGACGG AACACTTACT ACCTCGTCCT TTTGTGAGTC

AAGGACGAGA AAGGACAAAA ACATATTCAC TTAACAGCAG AGGTTACTTC AGAAAAGAAA   180
TTCCTGCTCT TTCCTGTTTT TGTATAAGTG AATTGTCGTC TCCAATGAAG TCTTTTCTTT

GAGGAGCACG TAGGAGCAAG ATTCTGCTGG TGAATACTAA AGGTCTTGAT GAACCCCACA   240
CTCCTCGTGC ATCCTCGTTC TAAGACGACC ACTTATGATT TCCAGAACTA CTTGGGGTGT

TTGGGCATGG TGATTTTCGC TTAGTAGCTG AACTATTTGA TTCCACCAGA ACACATACAA   300
AACCCGTACC ACTAAAAGCG AATCATCGAC TTGATAAACT AAGGTGGTCT TGTGTATGTT

ACAGAAAAGA GCCAGACATG AACAAAGTCA AGCTTTTCTC AACAGTTGCC CATGGAAACA   360
TGTCTTTTCT CGGTCTGTAC TTGTTTCAGT TCGAAAAGAG TTGTCAACGG GTACCTTTGT

AAAGTGCAAG AAGAAAAGCT TACAATGGTT CTAGAAGGAA TATTTTTCCT CGCCGTTCTT   420
TTTCACGTTC TTCTTTTCGA ATGTTACCAA GATCTTCCTT ATAAAAGGA GCGGCAAGAA

TTGATAAAAG AAATACAGAG GTTACTGAAA AGCCTGGTGC CAAGATGTTC TGGAACAATT   480
AACTATTTTC TTTATGTCTC CAATGACTTT TCGGACCACG GTTCTACAAG ACCTTGTTAA

TTTTGGTTAA AATGAATGGA GCCCCACAGA ATACAAGCCA TGGCAGTAAA GCACAGGAAA   540
AAAACCAATT TTACTTACCT CGGGGTGTCT TATGTTCGGT ACCGTCATTT CGTGTCCTTT

TAATGAAAGA AGCTTGCAAA ACCTTGTTTT TCACTCAGAA TATTGTACAT GAAAACTGTG   600
ATTACTTTCT TCGAACGTTT TGGAACAAAA AGTGAGTCTT ATAACATGTA CTTTTGACAC

ACAGGATGGT GATACAGAAC AATCTGTGCT TTGGTAAATG CATCTCTCTC CATGTTCCAA   660
TGTCCTACCA CTATGTCTTG TTAGACACGA AACCATTTAC GTAGAGAGAG GTACAAGGTT

ATCAGCAAGA TCGACGAAAT ACTTGTTCCC ATTGCTTGCC GTCCAAATTT ACCCTGAACC   720
TAGTCGTTCT AGCTGCTTTA TGAACAAGGG TAACGAACGG CAGGTTTAAA TGGGACTTGG

ACCTGACGCT GAATTGTACT GGATCTAAGA ATGTAGTAAA GGTTGTCATG ATGGTAGAGG   780
TGGACTGCGA CTTAACATGA CCTAGATTCT TACATCATTT CCAACAGTAC TACCATCTCC

AATGCACGTG TGAAGCTCAT AAGAGCAACT TCCACCAAAC TGCACAGTTT AACATGGATA   840
TTACGTGCAC ACTTCGAGTA TTCTCGTTGA AGGTGGTTTG ACGTGTCAAA TTGTACCTAT

CATCTACTAC CCTGCACCAT TAAAGGACTG CCATACAGTA TGGAAATGCC CTTTTGTTGG   900
GTAGATGATG GGACGTGGTA ATTTCCTGAC GGTATGTCAT ACCTTTACGG GAAAACAACC

AATATTTGTT ACATACTATG CATCTAAAGC ATTATGTTGC CTTCTATTTC ATATAACCAC   960
TTATAAACAA TGTATGATAC GTAGATTTCG TAATACAACG GAAGATAAAG TATATTGGTG

ATGGAATAAG GATTGTATGA ATTATAATTA ACAAATGGCA TTTTGTGTAA CATGCAAGAT  1020
TACCTTATTC CTAACATACT TAATATTAAT TGTTTACCGT AAAACACATT GTACGTTCTA
```

Figure 2A

```
CTCTGTTCCA TCAGTTGCAA GATAAAAGGC AATATTTGTT TGACTTTTTT TCTACAAAAT   1080
GAGACAAGGT AGTCAACGTT CTATTTTCCG TTATAAACAA ACTGAAAAAA AGATGTTTTA

GAATACCCAA ATATATGATA AGATAATGGG GTCAAAACTG TTAAGGGGTA ATGTAATAAT   1140
CTTATGGGTT TATATACTAT TCTATTACCC CAGTTTTGAC AATTCCCCAT TACATTATTA

AGGGACTAAG TTTGCCCAGG AGCAGTGACC CATAACAACC AATCAGCAGG TATGATTTAC   1200
TCCCTGATTC AAACGGGTCC TCGTCACTGG GTATTGTTGG TTAGTCGTCC ATACTAAATG

TGGTCACCTG TTTAAAAGCA AACATCTTAT TGGTTGCTAT GGGTTACTGC TTCTGGGCAA   1260
ACCAGTGGAC AAATTTTCGT TTGTAGAATA ACCAACGATA CCCAATGACG AAGACCCGTT

AATGTGTGCC TCATAGGGGG GTTAGTGTGT TGTGTACTGA ATAAATTGTA TTTATTTCAT   1320
TTACACACGG AGTATCCCCC CAATCACACA ACACATGACT TATTTAACAT AAATAAAGTA

TGTTACAAAA AAAAAAAA
ACAATGTTTT TTTTTTTT
```

Figure 2B

```
MSRTRKVDSL LLLAIPGLAL LLLPNAYCAS CEPVRIPMCK SMPWNMTKMP NHLHHSTQAN    60

AILAIEQFEG LLTTECSQDL LFFLCAMYAP ICTIDFQHEP IKPCKSVCER ARAGCEPILI   120

KYRHTWPESL ACEELPVYDR GVCISPEAIV TVEQGTDSMP DFSMDSNNGN CGSGREHCKC   180

KPMKATQKTY LKNNYNYVIR AKVKEVKVKC HDATAIVEVK EILKSSLVNI PKDTVTLYTN   240

SGCLCPQLVA NEEYIIMGYE DKERTRLLLV EGSLAEKWRD RLAKKVKRWD QKLRRPRKSK   300

DPVAPIPNKN SNSRQARS
```

Figure 3

```
GAATTCCCTT TCACACAGGA CTCCTGGCAG AGGTGAATGG TTAGCCCTAT GGATTTGGTT    60
CTTAAGGGAA AGTGTGTCCT GAGGACCGTC TCCACTTACC AATCGGGATA CCTAAACCAA

TGTTGATTTT GACACATGAT TGATTGCTTT CAGATAGGAT TGAAGGACTT GGATTTTTAT   120
ACAACTAAAA CTGTGTACTA ACTAACGAAA GTCTATCCTA ACTTCCTGAA CCTAAAAATA

CTAATTCTGC ACTTTTAAAT TATCTGAGTA ATTGTTCATT TTGTATTGGA TGGGACTAAA   180
GATTAAGACG TGAAAATTTA ATAGACTCAT TAACAAGTAA AACATAACCT ACCCTGATTT

GATAAACTTA ACTCCTTGCT TTTGACTTGC CCATAAACTA TAAGGTGGGG TGAGTTGTAG   240
CTATTTGAAT TGAGGAACGA AAACTGAACG GGTATTTGAT ATTCCACCCC ACTCAACATC

TTGCTTTTAC ATGTGCCCAG ATTTTCCCTG TATTCCCTGT ATTCCCTCTA AAGTAAGCCT   300
AACGAAAATG TACACGGGTC TAAAAGGGAC ATAAGGGACA TAAGGGAGAT TTCATTCGGA

ACACATACAG GTTGGGCAGA ATAACAATGT CTCGAACAAG GAAAGTGGAC TCATTACTGC   360
TGTGTATGTC CAACCCGTCT TATTGTTACA GAGCTTGTTC CTTTCACCTG AGTAATGACG

TACTGGCCAT ACCTGGACTG GCGCTTCTCT TATTACCCAA TGCTTACTGT GCTTCGTGTG   420
ATGACCGGTA TGGACCTGAC CGCGAAGAGA ATAATGGGTT ACGAATGACA CGAAGCACAC

AGCCTGTGCG GATCCCCATG TGCAAATCTA TGCCATGGAA CATGACCAAG ATGCCCAACC   480
TCGGACACGC CTAGGGGTAC ACGTTTAGAT ACGGTACCTT GTACTGGTTC TACGGGTTGG

ATCTCCACCA CAGCACTCAA GCCAATGCCA TCCTGGCAAT GAACAGTTT GAAGGTTTGC    540
TAGAGGTGGT GTCGTGAGTT CGGTTACGGT AGGACCGTTA ACTTGTCAAA CTTCCAAACG

TGACCACTGA ATGTAGCCAG GACCTTTTGT TCTTTCTGTG TGCCATGTAT GCCCCCATTT   600
ACTGGTGACT TACATCGGTC CTGGAAAACA AGAAAGACAC ACGGTACATA CGGGGGTAAA

GTACCATCGA TTTCCAGCAT GAACCAATTA AGCCTTGCAA GTCCGTGTGC GAAAGGGCCA   660
CATGGTAGCT AAAGGTCGTA CTTGGTTAAT TCGGAACGTT CAGGCACACG CTTTCCCGGT

GGGCCGGCTG TGAGCCCATT CTCATAAAGT ACCGGCACAC TTGGCCAGAG AGCCTGGCAT   720
CCCGGCCGAC ACTCGGGTAA GAGTATTTCA TGGCCGTGTG AACCGGTCTC TCGGACCGTA

GTGAAGAGCT GCCCGTATAT GACAGAGGAG TCTGCATCTC CCCAGAGGCT ATCGTCACAG   780
CACTTCTCGA CGGGCATATA CTGTCTCCTC AGACGTAGAG GGGTCTCCGA TAGCAGTGTC

TGGAACAAGG AACAGATTCA ATGCCAGACT TCTCCATGGA TTCAAACAAT GGAAATTGCG   840
ACCTTGTTCC TTGTCTAAGT TACGGTCTGA AGAGGTACCT AAGTTTGTTA CCTTTAACGC

GAAGCGGCAG GGAGCACTGT AAATGCAAGC CCATGAAGGC AACCCAAAAG ACGTATCTCA   900
CTTCGCCGTC CCTCGTGACA TTTACGTTCG GGTACTTCCG TTGGGTTTTC TGCATAGAGT

AGAATAATTA CAATTATGTA ATCAGAGCAA AAGTGAAAGA GGTGAAAGTG AAATGCCACG    960
TCTTATTAAT GTTAATACAT TAGTCTCGTT TTCACTTTCT CCACTTTCAC TTTACGGTGC

ACGCAACAGC AATTGTGGAA GTAAAGGAGA TTCTCAAGTC TTCCCTAGTG AACATTCCTA   1020
TGCGTTGTCG TTAACACCTT CATTTCCTCT AAGAGTTCAG AAGGGATCAC TTGTAAGGAT
```

Figure 4A

```
AAGACACAGT GACACTGTAC ACCAACTCAG GCTGCTTGTG CCCCCAGCTT GTTGCCAATG   1080
TTCTGTGTCA CTGTGACATG TGGTTGAGTC CGACGAACAC GGGGGTCGAA CAACGGTTAC

AGGAATACAT AATTATGGGC TATGAAGACA AAGAGCGTAC CAGGCTTCTA CTAGTGGAAG   1140
TCCTTATGTA TTAATACCCG ATACTTCTGT TTCTCGCATG GTCCGAAGAT GATCACCTTC

GATCCTTGGC CGAAAAATGG AGAGATCGTC TTGCTAAGAA AGTCAAGCGC TGGGATCAAA   1200
CTAGGAACCG GCTTTTTACC TCTCTAGCAG AACGATTCTT TCAGTTCGCG ACCCTAGTTT

AGCTTCGACG TCCCAGGAAA AGCAAAGACC CCGTGGCTCC AATTCCCAAC AAAAACAGCA   1260
TCGAAGCTGC AGGGTCCTTT TCGTTTCTGG GGCACCGAGG TTAAGGGTTG TTTTTGTCGT

ATTCCAGACA AGCGCGTAGT TAGACTAACG GAAAGGTGTA TGGAAACTCT ATGGACTTTG   1320
TAAGGTCTGT TCGCGCATCA ATCTGATTGC CTTTCCACAT ACCTTTGAGA TACCTGAAAC

AAACTAAGAT TTGCATTGTT GGAAGAGCAA AAAAGAAATT GCACTACAGC ACGTTATATT   1380
TTTGATTCTA AACGTAACAA CCTTCTCGTT TTTTCTTTAA CGTGATGTCG TGCAATATAA

CTATTGTTTA CTACAAGAAG CTGGTTTAGT TGATTGTAGT TCTCCTTTCC TTCTTTTTTT   1440
GATAACAAAT GATGTTCTTC GACCAAATCA ACTAACATCA AGAGGAAAGG AAGAAAAAAA

TTATAACTAT ATTTGCACGT GTTCCCAGGC AATTGTTTTA TTCAACTTCC AGTGACAGAG   1500
AATATTGATA TAAACGTGCA CAAGGGTCCG TTAACAAAAT AAGTTGAAGG TCACTGTCTC

CAGTGACTGA ATGTCTCAGC CTAAAGAAGC TCAATTCATT TCTGATCAAC TAATGGTGAC   1560
GTCACTGACT TACAGAGTCG GATTTCTTCG AGTTAAGTAA AGACTAGTTG ATTACCACTG

AAGTGTTTGA TACTTGGGGA AAGTGAACTA ATTGCAATGG TAAATCAGAG AAAAGTTGAC   1620
TTCACAAACT ATGAACCCCT TTCACTTGAT TAACGTTACC ATTTAGTCTC TTTTCAACTG

CAATGTTGCT TTTCCTGTAG ATGAACAAGT GAGAGATCAC ATTTAAATGA TGATCACTTT   1680
GTTACAACGA AAAGGACATC TACTTGTTCA CTCTCTAGTG TAAATTTACT ACTAGTGAAA

CCATTTAATA CTTTCAGCAG TTTTAGTTAG ATGACATGTA GGATGCACCT AAATCTAAAT   1740
GGTAAATTAT GAAAGTCGTC AAAATCAATC TACTGTACAT CCTACGTGGA TTTAGATTTA

ATTTTATCAT AAATGAAGAG CTGGTTTAGA CTGTATGGTC ACTGTTGGGA AGGTAAATGC   1800
TAAAATAGTA TTTACTTCTC GACCAAATCT GACATACCAG TGACAACCCT TCCATTTACG

CTACTTTGTC AATTCTGTTT TAAAAATTGC CTAAATAAAT ATTAAGTCCT AAATAAAAAA   1860
GATGAAACAG TTAAGACAAA ATTTTAACG GATTTATTTA TAATTCAGGA TTTATTTTTT

AAAAAAAAAA AAAAA
TTTTTTTTTT TTTTT
```

Figure 4B

| | | | | | | |
|---|---|---|---|---|---|---|
| MLLLFRAIPM | LLLGLMVLQT | DCEIAQYYID | EEEPPGTVIA | VLSQHSIFNT | TDIPATNFRL | 60 |
| MKQFNNSLIG | VRESDGQLSI | MERIDREQIC | RQSLHCNLAL | DVVSFSKGHF | KLLNVKVEVR | 120 |
| DINDHSPHFP | SEIMHVEVSE | SSSVGTRIPL | EIAIDEDVGS | NSIQNFQISN | NSHFSIDVLT | 180 |
| RADGVKYADL | VLMRELDREI | QPTYIMELLA | MDGGVPSLSG | TAVVNIRVLD | FNDNSPVFER | 240 |
| STIAVDLVED | APLGYLLLEL | HATDDDEGVN | GEIVYGFSTL | ASQEVRQLFK | INSRTGSVTL | 300 |
| EGQVDFETKQ | TYEFEVQAQD | LGPNPLTATC | KVTVHILDVN | DNTPAITITP | LTTVNAGVAY | 360 |
| IPETATKENF | IALISTTDRA | SGSNGQVRCT | LYGHEHFKLQ | QAYEDSYMIV | TTSTLDRENI | 420 |
| AAYSLTVVAE | DLGFPSLKTK | KYYTVKVSDE | NDNAPVFSKP | QYEASILENN | APGSYITTVI | 480 |
| ARDSDSDQNG | KVNYRLVDAK | VMGQSLTTFV | SLDADSGVLR | AVRSLDYEKL | KQLDFEIEAA | 540 |
| DNGIPQLSTR | VQLNLRIVDQ | NDNCPVITNP | LLNNGSGEVL | LPISAPQNYL | VFQLKAEDSD | 600 |
| EGHNSQLFYT | ILRDPSRLFA | INKESGEVFL | KKQLNSDHSE | DLSIVVAVYD | LGRPSLSTNA | 660 |
| TVKFILTDSF | PSNVEVVILQ | PSAEEQHQID | MSIIFIAVLA | GGCALLLLAI | FFVACTCKKK | 720 |
| AGEFKQVPEQ | HGTCNEERLL | STPSPQSVSS | SLSQSESCQL | SINTESENCS | VSSNQEQHQQ | 780 |
| TGIKHSISVP | SYHTSGWHLD | NCAMSISGHS | HMGHISTKVQ | WAKEIVTSMT | VTLILVENQK | 840 |
| RRALSSQCRH | KPVLNTQMNQ | QGSDMPITIS | ATESTRVQKM | GTAHCNMKRA | IDCLTL | |

Figure 5

```
GAATTCCCAG AGATGAACTC CTTGAGATTG TTTTAAATGA CTGCAGGTCT GGAAGGATTC      60
CTTAAGGGTC TCTACTTGAG GAACTCTAAC AAAATTTACT GACGTCCAGA CCTTCCTAAG

ACATTGCCAC ACTGTTTCTA GGCATGAAAA AACTGCAAGT TTCAACTTTG TTTTGGTGC      120
TGTAACGGTG TGACAAAGAT CCGTACTTTT TTGACGTTCA AAGTTGAAAC AAAAACCACG

AACTTTGATT CTTCAAGATG CTGCTTCTCT TCAGAGCCAT TCCAATGCTG CTGTTGGGAC     180
TTGAAACTAA GAAGTTCTAC GACGAAGAGA AGTCTCGGTA AGGTTACGAC GACAACCCTG

TGATGGTTTT ACAAACAGAC TGTGAAATTG CCCAGTACTA CATAGATGAA GAAGAACCCC    240
ACTACCAAAA TGTTTGTCTG ACACTTTAAC GGGTCATGAT GTATCTACTT CTTCTTGGGG

CTGGCACTGT AATTGCAGTG TTGTCACAAC ACTCCATATT TAACACTACA GATATACCTG    300
GACCGTGACA TTAACGTCAC AACAGTGTTG TGAGGTATAA ATTGTGATGT CTATATGGAC

CAACCAATTT CCGTCTAATG AAGCAATTTA ATAATTCCCT TATCGGAGTC CGTGAGAGTG    360
GTTGGTTAAA GGCAGATTAC TTCGTTAAAT TATTAAGGGA ATAGCCTCAG GCACTCTCAC

ATGGGCAGCT GAGCATCATG GAGAGGATTG ACCGGGAGCA AATCTGCAGG CAGTCCCTTC    420
TACCCGTCGA CTCGTAGTAC CTCTCCTAAC TGGCCCTCGT TTAGACGTCC GTCAGGGAAG

ACTGCAACCT GGCTTTGGAT GTGGTCAGCT TTTCCAAAGG ACACTTCAAG CTTCTGAACG    480
TGACGTTGGA CCGAAACCTA CACCAGTCGA AAAGGTTTCC TGTGAAGTTC GAAGACTTGC

TGAAAGTGGA GGTGAGAGAC ATTAATGACC ATAGCCCTCA CTTTCCCAGT GAAATAATGC    540
ACTTTCACCT CCACTCTCTG TAATTACTGG TATCGGGAGT GAAAGGGTCA CTTTATTACG

ATGTGGAGGT GTCTGAAAGT TCCTCTGTGG GCACCAGGAT TCCTTTAGAA ATTGCAATAG   600
TACACCTCCA CAGACTTTCA AGGAGACACC CGTGGTCCTA AGGAAATCTT TAACGTTATC

ATGAAGATGT TGGGTCCAAC TCCATCCAGA ACTTTCAGAT CTCAAATAAT AGCCACTTCA    660
TACTTCTACA ACCCAGGTTG AGGTAGGTCT TGAAAGTCTA GAGTTTATTA TCGGTGAAGT

GCATTGATGT GCTAACCAGA GCAGATGGGG TGAAATATGC AGATTTAGTC TTAATGAGAG    720
CGTAACTACA CGATTGGTCT CGTCTACCCC ACTTTATACG TCTAAATCAG AATTACTCTC

AACTGGACAG GAAATCCAG CCAACATACA TAATGGAGCT ACTAGCAATG GATGGGGGTG   780
TTGACCTGTC CCTTTAGGTC GGTTGTATGT ATTACCTCGA TGATCGTTAC CTACCCCCAC

TACCATCACT ATCTGGTACT GCAGTGGTTA ACATCCGAGT CCTGGACTTT AATGATAACA    840
ATGGTAGTGA TAGACCATGA CGTCACCAAT TGTAGGCTCA GGACCTGAAA TTACTATTGT

GCCCAGTGTT TGAGAGAAGC ACCATTGCTG TGGACCTAGT AGAGGATGCT CCTCTGGGAT    900
CGGGTCACAA ACTCTCTTCG TGGTAACGAC ACCTGGATCA TCTCCTACGA GGAGACCCTA

ACCTTTTGTT GGAGTTACAT GCTACTGACG ATGATGAAGG AGTGAATGGA GAAATTGTTT    960
TGGAAAACAA CCTCAATGTA CGATGACTGC TACTACTTCC TCACTTACCT CTTTAACAAA

ATGGATTCAG CACTTTGGCA TCTCAAGAGG TACGTCAGCT ATTTAAAATT AACTCCAGAA   1020
TACCTAAGTC GTGAAACCGT AGAGTTCTCC ATGCAGTCGA TAAATTTTAA TTGAGGTCTT
```

Figure 6A

```
CTGGCAGTGT TACTCTTGAA GGCCAAGTTG ATTTTGAGAC CAAGCAGACT TACGAATTTG   1080
GACCGTCACA ATGAGAACTT CCGGTTCAAC TAAAACTCTG GTTCGTCTGA ATGCTTAAAC

AGGTACAAGC CCAAGATTTG GGCCCCAACC CACTGACTGC TACTTGTAAA GTAACTGTTC   1140
TCCATGTTCG GGTTCTAAAC CCGGGGTTGG GTGACTGACG ATGAACATTT CATTGACAAG

ATATACTTGA TGTAAATGAT AATACCCCAG CCATCACTAT TACCCCTCTG ACTACTGTAA   1200
TATATGAACT ACATTTACTA TTATGGGGTC GGTAGTGATA ATGGGGAGAC TGATGACATT

ATGCAGGAGT TGCCTATATT CCAGAAACAG CCACAAAGGA GAACTTTATA GCTCTGATCA   1260
TACGTCCTCA ACGGATATAA GGTCTTTGTC GGTGTTTCCT CTTGAAATAT CGAGACTAGT

GCACTACTGA CAGAGCCTCT GGATCTAATG GACAAGTTCG CTGTACTCTT TATGGACATG   1320
CGTGATGACT GTCTCGGAGA CCTAGATTAC CTGTTCAAGC GACATGAGAA ATACCTGTAC

AGCACTTTAA ACTACAGCAA GCTTATGAGG ACAGTTACAT GATAGTTACC ACCTCTACTT   1380
TCGTGAAATT TGATGTCGTT CGAATACTCC TGTCAATGTA CTATCAATGG TGGAGATGAA

TAGACAGGGA AAACATAGCA GCGTACTCTT TGACAGTAGT TGCAGAAGAC CTTGGCTTCC   1440
ATCTGTCCCT TTTGTATCGT CGCATGAGAA ACTGTCATCA ACGTCTTCTG GAACCGAAGG

CCTCATTGAA GACCAAAAAG TACTACACAG TCAAGGTTAG TGATGAGAAT GACAATGCAC   1500
GGAGTAACTT CTGGTTTTTC ATGATGTGTC AGTTCCAATC ACTACTCTTA CTGTTACGTG

CTGTATTTTC TAAACCCCAG TATGAAGCTT CTATTCTGGA AAATAATGCT CCAGGCTCTT   1560
GACATAAAAG ATTTGGGGTC ATACTTCGAA GATAAGACCT TTTATTACGA GGTCCGAGAA

ATATAACTAC AGTGATAGCC AGAGACTCTG ATAGTGATCA AAATGGCAAA GTAAATTACA   1620
TATATTGATG TCACTATCGG TCTCTGAGAC TATCACTAGT TTTACCGTTT CATTTAATGT

GACTTGTGGA TGCAAAAGTG ATGGGCCAGT CACTAACAAC ATTTGTTTCT CTTGATGCGG   1680
CTGAACACCT ACGTTTTCAC TACCCGGTCA GTGATTGTTG TAAACAAAGA GAACTACGCC

ACTCTGGAGT ATTGAGAGCT GTTAGGTCTT TAGACTATGA AAAACTTAAA CAACTGGATT   1740
TGAGACCTCA TAACTCTCGA CAATCCAGAA ATCTGATACT TTTTGAATTT GTTGACCTAA

TTGAAATTGA AGCTGCAGAC AATGGGATCC CTCAACTCTC CACTCGCGTT CAACTAAATC   1800
AACTTTAACT TCGACGTCTG TTACCCTAGG GAGTTGAGAG GTGAGCGCAA GTTGATTTAG

TCAGAATAGT TGATCAAAAT GATAATTGCC CTGTGATAAC TAATCCTCTT CTTAATAATG   1860
AGTCTTATCA ACTAGTTTTA CTATTAACGG GACACTATTG ATTAGGAGAA GAATTATTAC

GCTCGGGTGA AGTTCTGCTT CCCATCAGCG CTCCTCAAAA CTATTTAGTT TTCCAGCTCA   1920
CGAGCCCACT TCAAGACGAA GGGTAGTCGC GAGGAGTTTT GATAAATCAA AAGGTCGAGT

AAGCCGAGGA TTCAGATGAA GGGCACAACT CCCAGCTGTT CTATACCATA CTGAGAGATC   1980
TTCGGCTCCT AAGTCTACTT CCCGTGTTGA GGGTCGACAA GATATGGTAT GACTCTCTAG

CAAGCAGATT GTTTGCCATT AACAAAGAAA GTGGTGAAGT GTTCCTGAAA AAACAATTAA   2040
GTTCGTCTAA CAAACGGTAA TTGTTTCTTT CACCACTTCA CAAGGACTTT TTTGTTAATT

ACTCTGACCA TTCAGAGGAC TTGAGCATAG TAGTTGCAGT GTATGACTTG GGAAGACCTT   2100
TGAGACTGGT AAGTCTCCTG AACTCGTATC ATCAACGTCA CATACTGAAC CCTTCTGGAA

CATTATCCAC CAATGCTACA GTTAAATTCA TCCTCACCGA CTCTTTTCCT TCTAACGTTG   2160
GTAATAGGTG GTTACGATGT CAATTTAAGT AGGAGTGGCT GAGAAAAGGA AGATTGCAAC
```

Figure 6B

```
AAGTCGTTAT TTTGCAACCA TCTGCAGAAG AGCAGCACCA GATCGATATG TCCATTATAT    2220
TTCAGCAATA AAACGTTGGT AGACGTCTTC TCGTCGTGGT CTAGCTATAC AGGTAATATA

TCATTGCAGT GCTGGCTGGT GGTTGTGCTT TGCTACTTTT GGCCATCTTT TTTGTGGCCT    2280
AGTAACGTCA CGACCGACCA CCAACACGAA ACGATGAAAA CCGGTAGAAA AAACACCGGA

GTACTTGTAA AAAGAAAGCT GGTGAATTTA AGCAGGTACC TGAACAACAC GGAACATGCA    2340
CATGAACATT TTTCTTTCGA CCACTTAAAT TCGTCCATGG ACTTGTTGTG CCTTGTACGT

ATGAAGAACG CCTGTTAAGC ACCCCATCTC CCCAGTCGGT CTCTTCTTCT TTGTCTCAGT    2400
TACTTCTTGC GGACAATTCG TGGGGTAGAG GGGTCAGCCA GAGAAGAAGA AACAGAGTCA

CTGAGTCATG CCAACTCTCC ATCAATACTG AATCTGAGAA TTGCAGCGTG TCCTCTAACC    2460
GACTCAGTAC GGTTGAGAGG TAGTTATGAC TTAGACTCTT AACGTCGCAC AGGAGATTGG

AAGAGCAGCA TCAGCAAACA GGCATAAAGC ACTCCATCTC TGTACCATCT TATCACACAT    2520
TTCTCGTCGT AGTCGTTTGT CCGTATTTCG TGAGGTAGAG ACATGGTAGA ATAGTGTGTA

CTGGTTGGCA CCTGGACAAT TGTGCAATGA GCATAAGTGG ACATTCTCAC ATGGGGCACA    2580
GACCAACCGT GGACCTGTTA ACACGTTACT CGTATTCACC TGTAAGAGTG TACCCCGTGT

TTAGTACAAA GGTACAGTGG GCAAAGGAGA TAGTGACTTC AATGACAGTG ACTCTGATAC    2640
AATCATGTTT CCATGTCACC CGTTTCCTCT ATCACTGAAG TTACTGTCAC TGAGACTATG

TAGTGGAGAA TCAGAAAAGA AGAGCATTGA GCAGCCAATG CAGGCACAAG CCAGTGCTCA    2700
ATCACCTCTT AGTCTTTTCT TCTCGTAACT CGTCGGTTAC GTCCGTGTTC GGTCACGAGT

ATACACAGAT GAATCAGCAG GGTTCCGACA TGCCGATAAC TATTTCAGCC ACCGAATCAA    2760
TATGTGTCTA CTTAGTCGTC CCAAGGCTGT ACGGCTATTG ATAAAGTCGG TGGCTTAGTT

CAAGGGTCCA GAAAATGGGA ACTGCACATT GCAATATGAA AAGGGCTATA GACTGTCTTA    2820
GTTCCCAGGT CTTTTACCCT TGACGTGTAA CGTTATACTT TTCCCGATAT CTGACAGAAT

CTCTGTAGCT CCTGTATATT ACAATACCTA CCATGCAAGA ATGCCTAACC TGCACATACC    2880
GAGACATCGA GGACATATAA TGTTATGGAT GGTACGTTCT TACGGATTGG ACGTGTATGG

GAACCATACC CTTAGAGACC CTTATTACCA TATCAATAAT CCTGTTGCTA ATCGGATGCA    2940
CTTGGTATGG GAATCTCTGG GAATAATGGT ATAGTTATTA GGACAACGAT TAGCCTACGT

GGCGGAATAT GAAAGAGATT TAGTCAACAG AAGTGCAACG TTATCTCCGC AGAGATCGTC    3000
CCGCCTTATA CTTTCTCTAA ATCAGTTGTC TTCACGTTGC AATAGAGGCG TCTCTAGCAG

TAGCAGATAC CAAGAATTCA ATTACAGTCC GCAGATATCA AGACAGCTTC ATCCTTCAGA    3060
ATCGTCTATG GTTCTTAAGT TAATGTCAGG CGTCTATAGT TCTGTCGAAG TAGGAAGTCT

AATTGCTACA ACCTTTTAAT CATTAGGCAT GCAAGTGAGA ATGCACAAAG GCAAGTGCTT    3120
TTAACGATGT TGGAAAATTA GTAATCCGTA CGTTCACTCT TACGTGTTTC CGTTCACGAA

TAGCATGAAA GCTAAATATA TGGAGTCTCC CCTTTCCCTC TGATGGATGG GGGAGACAC     3180
ATCGTACTTT CGATTTATAT ACCTCAGAGG GGAAAGGGAG ACTACCTACC CCCCTCTGTG

AGGACAGTGC ATAAATATAC AGCTGCTTTC TATTTGCATT TCACTTGGGA ATTTTTTGTT    3240
TCCTGTCACG TATTTATATG TCGACGAAAG ATAAACGTAA AGTGAACCCT TAAAAAACAA

TTTTTTACAT ATTTATTTTT CCTGAATTGA ATGTGACATT GTCCTGTCAC CTAACTAGCA    3300
AAAAAATGTA TAAATAAAAA GGACTTAACT TACACTGTAA CAGGACAGTG GATTGATCGT
```

Figure 6C

```
ATTAAATCCA CAGACCTACA GTCAAATATT TGAGGGCCCC TGAAACAGCA CATCAGTCAG    3360
TAATTTAGGT GTCTGGATGT CAGTTTATAA ACTCCCGGGG ACTTTGTCGT GTAGTCAGTC

GACCTAAAGT GGCCTTTTTA CTTTTAGCAG CTCCTGGGTC TGCCCTCTGT GTTAATCAGC    3420
CTGGATTTCA CCGGAAAAAT GAAAATCGTC GAGGACCCAG ACGGAGACA CAATTAGTCG

CCCTGGTCAA GTCCTGAGTA GGATCATGGC GTTTTTATAT GCATCTCACC TACTTTGGAC    3480
GGGACCAGTT CAGGACTCAT CCTAGTACCG CAAAAATATA CGTAGAGTGG ATGAAACCTG

GTGATTTACA CATAATAGGA AACGCTTGGT TTCAGTGAAG TCTGTGTTGT ATATATTCTG    3540
CACTAAATGT GTATTATCCT TTGCGAACCA AAGTCACTTC AGACACAACA TATATAAGAC

TTATATACAC GCATTTTGTG TTTGTGTATA TATTTCAAGT CCATTCAGAT ATGTGTATAT    3600
AATATATGTG CGTAAAACAC AAACACATAT ATAAAGTTCA GGTAAGTCTA TACACATATA

AGTGCAGACC TTGTAAATTA AATATTCTGA TACTTTTTCC TCAATAAATA TTTAAAT
TCACGTCTGG AACATTTAAT TTATAAGACT ATGAAAAAGG AGTTATTTAT AAATTTA
```

Figure 6D

```
MVCCGPGRML  LGWAGLLVLA  ALCLLQVPGA  QAAACEPVRI  PLCKSLPWNM  TKMPNHLHHS      60

TQANAILAME  QFEGLLGTHC  SPDLLFFLCA  MYAPICTIDF  QHEPIKPCKS  VCERARQGCE     120

PILIKYRHSW  PESLACDELP  VYDRGVCISP  EAIVTADGAD  FPMDSSTGHC  RGASSERCKC     180

KPVRATQKTY  FRNNYNYVIR  AKVKEVKMKC  HDVTAVVEVK  EILKASLVNI  PRDTVNLYTT     240

SGCLCPPLTV  NEEYVIMGYE  DEERSRLLLV  EGSIAEKWKD  RLGKKVKRWD  MKLRHLGLGK     300

TDASDSTQNQ  KSGRNSNPRP  ARS.
```

Figure 7

```
AAGCCTGGGA CCATGGTCTG CTGCGGCCCG GGACGGATGC TGCTAGGATG GGCCGGGTTG      60
TTCGGACCCT GGTACCAGAC GACGCCGGGC CCTGCCTACG ACGATCCTAC CCGGCCCAAC

CTAGTCCTGG CTGCTCTCTG CCTGCTCCAG GTGCCCGGAG CTCAGGCTGC AGCCTGTGAG     120
GATCAGGACC GACGAGAGAC GGACGAGGTC CACGGGCCTC GAGTCCGACG TCGGACACTC

CCTGTCCGCA TCCCGCTGTG CAAGTCCCTT CCCTGGAACA TGACCAAGAT GCCCAACCAC     180
GGACAGGCGT AGGGCGACAC GTTCAGGGAA GGGACCTTGT ACTGGTTCTA CGGGTTGGTG

CTGCACCACA GCACCCAGGC TAACGCCATC CTGGCCATGG AACAGTTCGA AGGGCTGCTG     240
GACGTGGTGT CGTGGGTCCG ATTGCGGTAG GACCGGTACC TTGTCAAGCT TCCCGACGAC

GGCACCCACT GCAGCCCGGA TCTTCTCTTC TTCCTCTGTG CAATGTACGC ACCCATTTGC     300
CCGTGGGTGA CGTCGGGCCT AGAAGAGAAG AAGGAGACAC GTTACATGCG TGGGTAAACG

ACCATCGACT TCCAGCACGA GCCCATCAAG CCCTGCAAGT CTGTGTGTGA GCGCGCCCGA     360
TGGTAGCTGA AGGTCGTGCT CGGGTAGTTC GGGACGTTCA GACACACACT CGCGCGGGCT

CAGGGCTGCG AGCCCATTCT CATCAAGTAC CGCCACTCGT GGCCGGAAAG CTTGGCCTGC     420
GTCCCGACGC TCGGGTAAGA GTAGTTCATG GCGGTGAGCA CCGGCCTTTC GAACCGGACG

GACGAGCTGC CGGTGTACGA CCGCGGCGTG TGCATCTCTC CTGAGGCCAT CGTCACCGCG     480
CTGCTCGACG GCCACATGCT GGCGCCGCAC ACGTAGAGAG GACTCCGGTA GCAGTGGCGC

GACGGAGCGG ATTTTCCTAT GGATTCAAGT ACTGGACACT GCAGAGGGGC AAGCAGCGAA     540
CTGCCTCGCC TAAAAGGATA CCTAAGTTCA TGACCTGTGA CGTCTCCCCG TTCGTCGCTT

CGTTGCAAAT GTAAGCCTGT CAGAGCTACA CAGAAGACCT ATTTCCGGAA CAATTACAAC     600
GCAACGTTTA CATTCGGACA GTCTCGATGT GTCTTCTGGA TAAAGGCCTT GTTAATGTTG

TATGTCATCC GGGCTAAAGT TAAAGAGGTA AAGATGAAAT GTCATGATGT GACCGCCGTT     660
ATACAGTAGG CCCGATTTCA ATTTCTCCAT TTCTACTTTA CAGTACTACA CTGGCGGCAA

GTGGAAGTGA AGGAAATTCT AAAGGCATCA CTGGTAAACA TTCCAAGGGA CACCGTCAAT     720
CACCTTCACT TCCTTTAAGA TTTCCGTAGT GACCATTTGT AAGGTTCCCT GTGGCAGTTA

CTTTATACCA CCTCTGGCTG CCTCTGTCCT CCACTTACTG TCAATGAGGA ATATGTCATC     780
GAAATATGGT GGAGACCGAC GGAGACAGGA GGTGAATGAC AGTTACTCCT TATACAGTAG

ATGGGCTATG AAGACGAGGA ACGTTCCAGG TTACTCTTGG TAGAAGGCTC TATAGCTGAG     840
TACCCGATAC TTCTGCTCCT TGCAAGGTCC AATGAGAACC ATCTTCCGAG ATATCGACTC

AAGTGGAAGG ATCGGCTTGG TAAGAAAGTC AAGCGCTGGG ATATGAAACT CCGACACCTT     900
TTCACCTTCC TAGCCGAACC ATTCTTTCAG TTCGCGACCC TATACTTTGA GGCTGTGGAA

GGACTGGGTA AAACTGATGC TAGCGATTCC ACTCAGAATC AGAAGTCTGG CAGGAACTCT     960
CCTGACCCAT TTTGACTACG ATCGCTAAGG TGAGTCTTAG TCTTCAGACC GTCCTTGAGA
```

Figure 8A

```
AATCCCCGGC CAGCACGCAG CTAAATCCTG AAATGTAAAA GGCCACACCC ACGGACTCCC    1020
TTAGGGGCCG GTCGTGCGTC GATTTAGGAC TTTACATTTT CCGGTGTGGG TGCCTGAGGG

TTCTAAGACT GGCGCTGGTG GACTAACAAA GGAAAACCGC ACAGTTGTGC TCGTGACCGA    1080
AAGATTCTGA CCGCGACCAC CTGATTGTTT CCTTTTGGCG TGTCAACACG AGCACTGGCT

TTGTTTACCG CAGACACCGC GTGGCTACCG AAGTTACTTC CGGTCCCCTT TCTCCTGCTT    1140
AACAAATGGC GTCTGTGGCG CACCGATGGC TTCAATGAAG GCCAGGGGAA AGAGGACGAA

CTTAATGGCG TGGGGTTAGA TCCTTTAATA TGTTATATAT TCTGTTTCAT CAATCACGTG    1200
GAATTACCGC ACCCCAATCT AGGAAATTAT ACAATATATA AGACAAAGTA GTTAGTGCAC

GGGACTGTTC TTTTGCAACC AGAATAGTAA ATTAAATATG TTGATGCTAA GGTTTCTGTA    1260
CCCTGACAAG AAAACGTTGG TCTTATCATT TAATTTATAC AACTACGATT CCAAAGACAT

CTGGACTCCC TGGGTTTAAT TTGGTGTTCT GTACCCTGAT TGAGAATGCA ATGTTTCATG    1320
GACCTGAGGG ACCCAAATTA AACCACAAGA CATGGGACTA ACTCTTACGT TACAAAGTAC

TAAAGAGAGA ATCCTGGTCA TATCTCAAGA ACTAGATATT GCTGTAAGAC AGCCTCTGCT    1380
ATTTCTCTCT TAGGACCAGT ATAGAGTTCT TGATCTATAA CGACATTCTG TCGGAGACGA

GCTGCGCTTA TAGTCTTGTG TTTGTATGCC TTTGTCCATT TCCCTCATGC TGTGAAAGTT    1440
CGACGCGAAT ATCAGAACAC AAACATACGG AAACAGGTAA AGGGAGTACG ACACTTTCAA

ATACATGTTT ATAAAGGTAG AACGGCATTT TGAAATCAGA CACTGCACAA GCAGAGTAGC    1500
TATGTACAAA TATTTCCATC TTGCCGTAAA ACTTTAGTCT GTGACGTGTT CGTCTCATCG

CCAACACCAG GAAGCATTTA TGAGGAAACG CCACACAGCA TGACTTATTT TCAAGATTGG    1560
GGTTGTGGTC CTTCGTAAAT ACTCCTTTGC GGTGTGTCGT ACTGAATAAA AGTTCTAACC

CAGGCAGCAA AATAAATAGT GTTGGGAGCC AAGAAAAGAA TATTTTGCCT GGTTAAGGGG    1620
GTCCGTCGTT TTATTTATCA CAACCCTCGG TTCTTTTCTT ATAAAACGGA CCAATTCCCC

CACACTGGAA TCAGTAGCCC TTGAGCCATT AACAGCAGTG TTCTTCTGGC AAGTTTTTGA    1680
GTGTGACCTT AGTCATCGGG AACTCGGTAA TTGTCGTCAC AAGAAGACCG TTCAAAAACT

TTTGTTCATA AATGTATTCA CGAGCATTAG AGATGAACTT ATAACTAGAC ATCTGTTGTT    1740
AAACAAGTAT TTACATAAGT GCTCGTAATC TCTACTTGAA TATTGATCTG TAGACAACAA

ATCTCTATAG CTCTGCTTCC TTCTAAATCA AACCCATTGT TGGATGCTCC CTCTCCATTC    1800
TAGAGATATC GAGACGAAGG AAGATTTAGT TTGGGTAACA ACCTACGAGG GAGAGGTAAG
```

Figure 8B

```
ATAAATAAAT TTGGCTTGCT GTATTGGCCA GGAAAAGAAA GTATTAAAGT ATGCATGCAT    1860
TATTTATTTA AACCGAACGA CATAACCGGT CCTTTTCTTT CATAATTTCA TACGTACGTA

GTGCACCAGG GTGTTATTTA ACAGAGGTAT GTAACTCTAT AAAAGACTAT AATTTACAGG    1920
CACGTGGTCC CACAATAAAT TGTCTCCATA CATTGAGATA TTTTCTGATA TTAAATGTCC

ACACGGAAAT GTGCACATTT GTTTACTTTT TTTCTTCCTT TTGCTTTGGG CTTGTGATTT    1980
TGTGCCTTTA CACGTGTAAA CAAATGAAAA AAAGAAGGAA AACGAAACCC GAACACTAAA

TGGTTTTTGG TGTGTTTATG TCTGTATTTT GGGGGGTGGG TAGGTTTAAG CCATTGCACA    2040
ACCAAAAACC ACACAAATAC AGACATAAAA CCCCCCACCC ATCCAAATTC GGTAACGTGT

TTCAAGTTGA ACTAGATTAG AGTAGACTAG GCTCATTGGC CTAGACATTA TGATTTGAAT    2100
AAGTTCAACT TGATCTAATC TCATCTGATC CGAGTAACCG GATCTGTAAT ACTAAACTTA

TTGTGTTGTT TAATGCTCCA TCAAGATGTC TAATAAAAGG AATATGGTTG TCAACAGAGA    2160
AACACAACAA ATTACGAGGT AGTTCTACAG ATTATTTTCC TTATACCAAC AGTTGTCTCT

CGACAACAAC AACAAA
GCTGTTGTTG TTGTTT
```

Figure 8C

| | | | | | | |
|---|---|---|---|---|---|---|
| MVCGSPGGML | LLRAGLLALA | ALCLLRVPGA | RAAACEPVRI | PLCKSLPWNM | TKMPNHLHHS | 60 |
| TQANAILAIE | QFEGLLGTHC | SPDLLFFLCA | MYAPICTIDF | QHEPIKPCKS | VCERARQGCE | 120 |
| PILIKYRHSW | PENLACEELP | VYDRGVCISP | EAIVTADGAD | FPMDSSNGNC | RGASSERCKC | 180 |
| KPIRATQKTY | FRNNYNYVIR | AKVKEIKTKC | HDVTAVVEVK | EILKSSLVNI | PRDTVNLYTS | 240 |
| SGCLCPPLNV | NEEYIIMGYE | DEERSRLLLV | EGSIAEKWKD | RLGKKVKRWD | MKLRHLGLSK | 300 |
| SDSSNSDSTQ | SQKSGRNSNP | RQARN. | | | | |

Figure 9

```
GGCGGAGCGG  GCCTTTTGGC  GTCCACTGCG  CGGCTGCACC  CTGCCCCATC  TGCCGGGATC    60
CCGCCTCGCC  CGGAAAACCG  CAGGTGACGC  GCCGACGTGG  GACGGGGTAG  ACGGCCCTAG

ATGGTCTGCG  GCAGCCCGGG  AGGGATGCTG  CTGCTGCGGG  CCGGGCTGCT  TGCCCTGGCT   120
TACCAGACGC  CGTCGGGCCC  TCCCTACGAC  GACGACGCCC  GGCCCGACGA  ACGGGACCGA

GCTCTCTGCC  TGCTCCGGGT  GCCCGGGGCT  CGGGCTGCAG  CCTGTGAGCC  CGTCCGCATC   180
CGAGAGACGG  ACGAGGCCCA  CGGGCCCCGA  GCCCGACGTC  GGACACTCGG  GCAGGCGTAG

CCCCTGTGCA  AGTCCCTGCC  CTGGAACATG  ACTAAGATGC  CAACCACCT   GCACCACAGC   240
GGGGACACGT  TCAGGGACGG  GACCTTGTAC  TGATTCTACG  GGTTGGTGGA  CGTGGTGTCG

ACTCAGGCCA  ACGCCATCCT  GGCCATCGAG  CAGTTCGAAG  GTCTGCTGGG  CACCCACTGC   300
TGAGTCCGGT  TGCGGTAGGA  CCGGTAGCTC  GTCAAGCTTC  CAGACGACCC  GTGGGTGACG

AGCCCCGATC  TGCTCTTCTT  CCTCTGTGCC  ATGTACGCGC  CCATCTGCAC  CATTGACTTC   360
TCGGGGCTAG  ACGAGAAGAA  GGAGACACGG  TACATGCGCG  GGTAGACGTG  GTAACTGAAG

CAGCACGAGC  CCATCAAGCC  CTGTAAGTCT  GTGTGCGAGC  GGGCCCGGCA  GGGCTGTGAG   420
GTCGTGCTCG  GGTAGTTCGG  GACATTCAGA  CACACGCTCG  CCCGGGCCGT  CCCGACACTC

CCCATACTCA  TCAAGTACCG  CCACTCGTGG  CCGGAGAACC  TGGCCTGCGA  GGAGCTGCCA   480
GGGTATGAGT  AGTTCATGGC  GGTGAGCACC  GGCCTCTTGG  ACCGGACGCT  CCTCGACGGT

GTGTACGACA  GGGGCGTGTG  CATCTCTCCC  GAGGCCATCG  TTACTGCGGA  CGGAGCTGAT   540
CACATGCTGT  CCCCGCACAC  GTAGAGAGGG  CTCCGGTAGC  AATGACGCCT  GCCTCGACTA

TTTCCTATGG  ATTCTAGTAA  CGGAAACTGT  AGAGGGCAA   GCAGTGAACG  CTGTAAATGT   600
AAAGGATACC  TAAGATCATT  GCCTTTGACA  TCTCCCCGTT  CGTCACTTGC  GACATTTACA

AAGCCTATTA  GAGCTACACA  GAAGACCTAT  TTCCGGAACA  ATTACAACTA  TGTCATTCGG   660
TTCGGATAAT  CTCGATGTGT  CTTCTGGATA  AAGGCCTTGT  TAATGTTGAT  ACAGTAAGCC

GCTAAAGTTA  AAGAGATAAA  GACTAAGTGC  CATGATGTGA  CTGCAGTAGT  GGAGGTGAAG   720
CGATTTCAAT  TTCTCTATTT  CTGATTCACG  GTACTACACT  GACGTCATCA  CCTCCACTTC

GAGATTCTAA  AGTCCTCTCT  GGTAAACATT  CCACGGGACA  CTGTCAACCT  CTATACCAGC   780
CTCTAAGATT  TCAGGAGAGA  CCATTTGTAA  GGTGCCCTGT  GACAGTTGGA  GATATGGTCG

TCTGGCTGCC  TCTGCCCTCC  ACTTAATGTT  AATGAGGAAT  ATATCATCAT  GGGCTATGAA   840
AGACCGACGG  AGACGGGAGG  TGAATTACAA  TTACTCCTTA  TATAGTAGTA  CCCGATACTT
```

Figure 10A

```
GATGAGGAAC GTTCCAGATT ACTCTTGGTG GAAGGCTCTA TAGCTGAGAA GTGGAAGGAT   900
CTACTCCTTG CAAGGTCTAA TGAGAACCAC CTTCCGAGAT ATCGACTCTT CACCTTCCTA

CGACTCGGTA AAAAAGTTAA GCGCTGGGAT ATGAAGCTTC GTCATCTTGG ACTCAGTAAA   960
GCTGAGCCAT TTTTTCAATT CGCGACCCTA TACTTCGAAG CAGTAGAACC TGAGTCATTT

AGTGATTCTA GCAATAGTGA TTCCACTCAG AGTCAGAAGT CTGGCAGGAA CTCGAACCCC  1020
TCACTAAGAT CGTTATCACT AAGGTGAGTC TCAGTCTTCA GACCGTCCTT GAGCTTGGGG

CGGCAAGCAC GCAACTAAAT CCCGAAATAC AAAAAGTAAC ACAGTGGACT TCCTATTAAG  1080
GCCGTTCGTG CGTTGATTTA GGGCTTTATG TTTTTCATTG TGTCACCTGA AGGATAATTC

ACTTACTTGC ATTGCTGGAC TAGCAAAGGA AAATTGCACT ATTGCACATC ATATTCTATT  1140
TGAATGAACG TAACGACCTG ATCGTTTCCT TTTAACGTGA TAACGTGTAG TATAAGATAA

GTTTACTATA AAAATCATGT GATAACTGAT TATTACTTCT GTTTCTCTTT TGGTTTCTGC  1200
CAAATGATAT TTTTAGTACA CTATTGACTA ATAATGAAGA CAAAGAGAAA ACCAAAGACG

TTCTCTCTTC TCTCAACCCC TTTGTAATGG TTTGGGGGCA GACTCTTAAG TATATTGTGA  1260
AAGAGAGAAG AGAGTTGGGG AAACATTACC AAACCCCCGT CTGAGAATTC ATATAACACT

GTTTTCTATT TCACTAATCA TGAGAAAAAC TGTTCTTTTG CAATAATAAT AAATTAAACA  1320
CAAAAGATAA AGTGATTAGT ACTCTTTTTG ACAAGAAAAC GTTATTATTA TTTAATTTGT

TGCTGTTACC AGAGCCTCTT TGCTGAGTCT CCAGATGTTA ATTTACTTTC TGCACCCCAA  1380
ACGACAATGG TCTCGGAGAA ACGACTCAGA GGTCTACAAT TAAATGAAAG ACGTGGGGTT

TTGGGAATGC AATATTGGAT GAAAGAGAG GTTCTGGTA TTCACAGAAA GCTAGATATG  1440
AACCCTTACG TTATAACCTA CTTTTCTCTC CAAAGACCAT AAGTGTCTTT CGATCTATAC

CCTTAAAACA TACTCTGCCG ATCTAATTAC AGCCTTATTT TTGTATGCCT TTTGGGCATT  1500
GGAATTTTGT ATGAGACGGC TAGATTAATG TCGGAATAAA AACATACGGA AAACCCGTAA

CTCCTCATGC TTAGAAAGTT CCAAATGTTT ATAAAGGTAA AATGGCAGTT TGAAGTCAAA  1560
GAGGAGTACG AATCTTTCAA GGTTTACAAA TATTTCCATT TTACCGTCAA ACTTCAGTTT

TGTCACATAG GCAAAGCAAT CAAGCACCAG GAAGTGTTTA TGAGGAAACA ACACCCAAGA  1620
ACAGTGTATC CGTTTCGTTA GTTCGTGGTC CTTCACAAAT ACTCCTTTGT TGTGGGTTCT

TGAATTATTT TTGAGACTGT CAGGAAGTAA AATAAATAGG AGCTTAAGAA AGAACATTTT  1680
ACTTAATAAA AACTCTGACA GTCCTTCATT TTATTTATCC TCGAATTCTT TCTTGTAAAA

GCCTGATTGA GAAGCACAAC TGAAACCAGT AGCCGCTGGG GTGTTAATGG TAGCATTCTT  1740
CGGACTAACT CTTCGTGTTG ACTTTGGTCA TCGGCGACCC CACAATTACC ATCGTAAGAA

CTTTTGGCAA TACATTTGAT TTGTTCATGA ATATATTAAT CAGCATTAGA GAAATGAATT  1800
GAAAACCGTT ATGTAAACTA AACAAGTACT TATATAATTA GTCGTAATCT CTTTACTTAA

ATAACTAGAC ATCTGCTGTT ATCACCATAG TTTTGTTTAA TTTGCTTCCT TTTAAATAAA  1860
TATTGATCTG TAGACGACAA TAGTGGTATC AAAACAAATT AAACGAAGGA AAATTTATTT

CCCATTGGTG AAAGTCAAAA AAAAAAAAA AAA
GGGTAACCAC TTTCAGTTTT TTTTTTTTT TTT
```

Figure 10B ized by UV irradiation.

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 270 amino acids
      (B) TYPE: amino acid
      (D) TOPOLOGY: linear (ii) MOLECULE TYPE: peptide (xi) SEQUENCE DESCRIPTION: SEQ ID NO:1:

```
Met Leu Leu Asn Val Leu Arg Ile Cys Ile Ile Val Cys Leu Val Asn
1               5                   10                  15

Asp Gly Ala Gly Lys His Ser Glu Gly Arg Glu Arg Thr Lys Thr Tyr
            20                  25                  30

Ser Leu Asn Ser Arg Gly Tyr Phe Arg Lys Glu Arg Gly Ala Arg Arg
        35                  40                  45

Ser Lys Ile Leu Leu Val Asn Thr Lys Gly Leu Asp Glu Pro His Ile
    50                  55                  60

Gly His Gly Asp Phe Gly Leu Val Ala Glu Leu Phe Asp Ser Thr Arg
65                  70                  75                  80
```

```
        Thr His Thr Asn Arg Lys Glu Pro Asp Met Asn Lys Val Lys Leu Phe
                         85                  90                  95

Ser Thr Val Ala His Gly Asn Lys Ser Ala Arg Arg Lys Ala Tyr Asn
                    100                 105                 110

Gly Ser Arg Arg Asn Ile Phe Ser Arg Arg Ser Phe Asp Lys Arg Asn
                    115                 120                 125

Thr Glu Val Thr Glu Lys Pro Gly Ala Lys Met Phe Trp Asn Asn Phe
                130                 135                 140

Leu Val Lys Met Asn Gly Ala Pro Gln Asn Thr Ser His Gly Ser Lys
        145                 150                 155                 160

Ala Gln Glu Ile Met Lys Glu Ala Cys Lys Thr Leu Pro Phe Thr Gln
                        165                 170                 175

Asn Ile Val His Glu Asn Cys Asp Arg Met Val Ile Gln Asn Asn Leu
                    180                 185                 190

Cys Phe Gly Lys Cys Ile Ser Leu His Val Pro Asn Gln Gln Asp Arg
                    195                 200                 205

Arg Asn Thr Cys Ser His Cys Leu Pro Ser Lys Phe Thr Leu Asn His
                    210                 215                 220

Leu Thr Leu Asn Cys Thr Gly Ser Lys Asn Val Val Lys Val Val Met
        225                 230                 235                 240

Met Val Glu Glu Cys Thr Cys Glu Ala His Lys Ser Asn Phe His Gln
                        245                 250                 255

Thr Ala Gln Phe Asn Met Asp Ser Thr Thr Leu His His
                        260                 265                 270

(2) INFORMATION FOR SEQ ID NO:2:

(i) SEQUENCE CHARACTERISTICS:
            (A) LENGTH: 1411 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:2:

GAATTCCTAA AAGCGGCACA GTGCAGGAAC AGCAAGTCGC TCAGAAACAC TGCAGGGTCT      60

AGATATCATA CAATGTTACT AAATGTACTC AGGATCTGTA TTATCGTCTG CCTTGTGAAT     120

GATGGAGCAG GAAAACACTC AGAAGGACGA GAAAGGACAA AAACATATTC ACTTAACAGC     180

AGAGGTTACT TCAGAAAAGA AAGAGGAGCA CGTAGGAGCA AGATTCTGCT GGTGAATACT     240

AAAGGTCTTG ATGAACCCCA CATTGGGCAT GGTGATTTTG GCTTAGTAGC TGAACTATTT     300

GATTCCACCA GAACACATAC AAACAGAAAA GAGCCAGACA TGAACAAAGT CAAGCTTTTC     360

TCAACAGTTG CCCATGGAAA CAAAAGTGCA AGAAGAAAAG CTTACAATGG TTCTAGAAGG     420

AATATTTTTT CTCGCCGTTC TTTTGATAAA AGAAATACAG AGGTTACTGA AAAGCCTGGT     480

GCCAAGATGT TCTGGAACAA TTTTTTGGTT AAAATGAATG GAGCCCCACA GAATACAAGC     540

CATGGCAGTA AGCACAGGA ATAATGAAA GAAGCTTGCA AAACCTTGCC CTTCACTCAG     600

AATATTGTAC ATGAAAACTG TGACAGGATG GTGATACAGA ACAATCTGTG CTTTGGTAAA     660

TGCATCTCTC TCCATGTTCC AAATCAGCAA GATCGACGAA ATACTTGTTC CCATTGCTTG     720

CCGTCCAAAT TTACCCTGAA CCACCTGACG CTGAATTGTA CTGGATCTAA GAATGTAGTA     780

AAGGTTGTCA TGATGGTAGA GGAATGCACG TGTGAAGCTC ATAAGAGCAA CTTCCACCAA     840

ACTGCACAGT TTAACATGGA TACATCTACT ACCCTGCACC ATTAAAAGGA CTGTCTGCCA     900
```

```
TACAGTATGG AAATGCCCAT TTGTTGGAAT ATTCGTTACA TGCTATGTAT CTAAAGCATT      960

ATGTTGCCTT CTGTTTCATA TAACCACATG GAATAAGGAT TGTATGAATT ATAATTAACA     1020

AATGGCATTT TGTGTAACAT GCAAGATCTC TGTTCCATCA GTTGCAAGAT AAAAGGCAAT     1080

ATTTGTTTGA CTTTTTTCTA CAAAATGAAT ACCCAAATAT ATGATAAGAT AATGGGGTCA     1140

AAACTGTTAA GGGGTAATGT AATAATAGGG ACTAACAACC AATCAGCAGG TATGATTTAC     1200

TGGTCACCTG TTTAAAAGCA AACATCTTAT TGGTTGCTAT GGGTTACTGC TTCTGGGCAA     1260

AATGTGTGCC TCATAGGGGG GTTAGTGTGT TGTGTACTGA ATTAATTGTA TTTATTTCAT     1320

TGTTACAATG AAGAGGATGT CTATGTTTAT TTCACTTTTA TTAATGTACA ATAAATGTTC     1380

TTGTTTCTTT AAAAAAAAAA AAAAACTCGA G                                    1411

(2) INFORMATION FOR SEQ ID NO:3:

(i) SEQUENCE CHARACTERISTICS:
        (A) LENGTH: 318 amino acids
        (B) TYPE: amino acid
        (D) TOPOLOGY: linear (ii) MOLECULE TYPE: peptide (xi) SEQUENCE DESCRIPTION: SEQ ID NO:3:

Met Ser Arg Thr Arg Lys Val Asp Ser Leu Leu Leu Ala Ile Pro
1               5                  10                  15

Gly Leu Ala Leu Leu Leu Pro Asn Ala Tyr Cys Ala Ser Cys Glu
                20                  25                  30

Pro Val Arg Ile Pro Met Cys Lys Ser Met Pro Trp Asn Met Thr Lys
            35                  40                  45

Met Pro Asn His Leu His His Ser Thr Gln Ala Asn Ala Ile Leu Ala
        50                  55                  60

Ile Glu Gln Phe Glu Gly Leu Leu Thr Thr Glu Cys Ser Gln Asp Leu
65                  70                  75                  80

Leu Phe Phe Leu Cys Ala Met Tyr Ala Pro Ile Cys Thr Ile Asp Phe
                85                  90                  95

Gln His Glu Pro Ile Lys Pro Cys Lys Ser Val Cys Glu Arg Ala Arg
            100                 105                 110

Ala Gly Cys Glu Pro Ile Leu Ile Lys Tyr Arg His Thr Trp Pro Glu
        115                 120                 125

Ser Leu Ala Cys Glu Glu Leu Pro Val Tyr Asp Arg Gly Val Cys Ile
    130                 135                 140

Ser Pro Glu Ala Ile Val Thr Val Glu Gln Gly Thr Asp Ser Met Pro
145                 150                 155                 160

Asp Phe Ser Met Asp Ser Asn Asn Gly Asn Cys Gly Ser Gly Arg Glu
                165                 170                 175

His Cys Lys Cys Lys Pro Met Lys Ala Thr Gln Lys Thr Tyr Leu Lys
            180                 185                 190

Asn Asn Tyr Asn Tyr Val Ile Arg Ala Lys Val Lys Glu Val Lys Val
        195                 200                 205

Lys Cys His Asp Ala Thr Ala Ile Val Glu Val Lys Glu Ile Leu Lys
    210                 215                 220

Ser Ser Leu Val Asn Ile Pro Lys Asp Thr Val Thr Leu Tyr Thr Asn
225                 230                 235                 240

Ser Gly Cys Leu Cys Pro Gln Leu Val Ala Asn Glu Glu Tyr Ile Ile
                245                 250                 255
```

```
Met Gly Tyr Glu Asp Lys Glu Arg Thr Arg Leu Leu Val Glu Gly
        260                 265                 270

Ser Leu Ala Glu Lys Trp Arg Asp Arg Leu Ala Lys Lys Val Lys Arg
        275                 280                 285

Trp Asp Gln Lys Leu Arg Arg Pro Arg Lys Ser Lys Asp Pro Val Ala
        290                 295                 300

Pro Ile Pro Asn Lys Asn Ser Asn Ser Arg Gln Ala Arg Ser
305                 310                 315
```

(2) INFORMATION FOR SEQ ID NO:4:

(i) SEQUENCE CHARACTERISTICS:
        (A) LENGTH: 1875 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

```
GAATTCCCTT TCACACAGGA CTCCTGGCAG AGGTGAATGG TTAGCCCTAT GGATTTGGTT      60

TGTTGATTTT GACACATGAT TGATTGCTTT CAGATAGGAT TGAAGGACTT GGATTTTTAT     120

CTAATTCTGC ACTTTTAAAT TATCTGAGTA ATTGTTCATT TTGTATTGGA TGGGACTAAA     180

GATAAACTTA ACTCCTTGCT TTTGACTTGC CCATAAACTA TAAGGTGGGG TGAGTTGTAG     240

TTGCTTTTAC ATGTGCCCAG ATTTTCCCTG TATTCCCTGT ATTCCCTCTA AAGTAAGCCT     300

ACACATACAG GTTGGGCAGA ATAACAATGT CTCGAACAAG GAAAGTGGAC TCATTACTGC     360

TACTGGCCAT ACCTGGACTG GCGCTTCTCT TATTACCCAA TGCTTACTGT GCTTCGTGTG     420

AGCCTGTGCG GATCCCCATG TGCAAATCTA TGCCATGGAA CATGACCAAG ATGCCCAACC     480

ATCTCCACCA CAGCACTCAA GCCAATGCCA TCCTGGCAAT GAACAGTTTT GAAGGTTTGC     540

TGACCACTGA ATGTAGCCAG GACCTTTTGT TCTTTCTGTG TGCCATGTAT GCCCCCATTT     600

GTACCATCGA TTTCCAGCAT GAACCAATTA AGCCTTGCAA GTCCGTGTGC GAAAGGGCCA     660

GGGCCGGCTG TGAGCCCATT CTCATAAAGT ACCGGCACAC TTGGCCAGAG AGCCTGGCAT     720

GTGAAGAGCT GCCCGTATAT GACAGAGGAG TCTGCATCTC CCCAGAGGCT ATCGTCACAG     780

TGGAACAAGG AACAGATTCA ATGCCAGACT TCTCCATGGA TTCAAACAAT GGAAATTGCG     840

GAAGCGGCAG GGAGCACTGT AAATGCAAGC CCATGAAGGC AACCCAAAAG ACGTATCTCA     900

AGAATAATTA CAATTATGTA ATCAGAGCAA AGTGAAAGA GGTGAAAGTG AAATGCCACG     960

ACGCAACAGC AATTGTGGAA GTAAAGGAGA TTCTCAAGTC TTCCCTAGTG AACATTCCTA    1020

AAGACACAGT GACACTGTAC ACCAACTCAG GCTGCTTGTG CCCCCAGCTT GTTGCCAATG    1080

AGGAATACAT AATTATGGGC TATGAAGACA AAGAGCGTAC CAGGCTTCTA CTAGTGGAAG    1140

GATCCTTGGC CGAAAAATGG AGAGATCGTC TTGCTAAGAA AGTCAAGCGC TGGGATCAAA    1200

AGCTTCGACG TCCCAGGAAA AGCAAAGACC CCGTGGCTCC AATTCCCAAC AAAAACAGCA    1260

ATTCCAGACA AGCGCGTAGT TAGACTAACG GAAAGGTGTA TGGAAACTCT ATGGACTTTG    1320

AAACTAAGAT TTGCATTGTT GGAAGAGCAA AAAGAAATT GCACTACAGC ACGTTATATT    1380

CTATTGTTTA CTACAAGAAG CTGGTTTAGT TGATTGTAGT TCTCCTTTCC TTCTTTTTTT    1440

TTATAACTAT ATTTGCACGT GTTCCCAGGC AATTGTTTTA TTCAACTTCC AGTGACAGAG    1500

CAGTGACTGA ATGTCTCAGC CTAAAGAAGC TCAATTCATT TCTGATCAAC TAATGGTGAC    1560

AAGTGTTTGA TACTTGGGGA AAGTGAACTA ATTGCAATGG TAAATCAGAG AAAAGTTGAC    1620
```

-continued

```
CAATGTTGCT TTTCCTGTAG ATGAACAAGT GAGAGATCAC ATTTAAATGA TGATCACTTT    1680

CCATTTAATA CTTTCAGCAG TTTTAGTTAG ATGACATGTA GGATGCACCT AAATCTAAAT    1740

ATTTTATCAT AAATGAAGAG CTGGTTTAGA CTGTATGGTC ACTGTTGGGA AGGTAAATGC    1800

CTACTTTGTC AATTCTGTTT TAAAAATTGC CTAAATAAAT ATTAAGTCCT AAATAAAAAA    1860

AAAAAAAAAA AAAAA                                                     1875
```

(2) INFORMATION FOR SEQ ID NO:5:

(i) SEQUENCE CHARACTERISTICS:
        (A) LENGTH: 979 amino acids
        (B) TYPE: amino acid
        (D) TOPOLOGY: linear (ii) MOLECULE TYPE: peptide (xi) SEQUENCE DESCRIPTION: SEQ ID NO:5:

```
Met Leu Leu Leu Phe Arg Ala Ile Pro Met Leu Leu Gly Leu Met
1               5                   10                  15

Val Leu Gln Thr Asp Cys Glu Ile Ala Gln Tyr Tyr Ile Asp Glu Glu
                20                  25                  30

Glu Pro Pro Gly Thr Val Ile Ala Val Leu Ser Gln His Ser Ile Phe
                35                  40                  45

Asn Thr Thr Asp Ile Pro Ala Thr Asn Phe Arg Leu Met Lys Gln Phe
        50                  55                  60

Asn Asn Ser Leu Ile Gly Val Arg Glu Ser Asp Gly Gln Leu Ser Ile
65                  70                  75                  80

Met Glu Arg Ile Asp Arg Glu Gln Ile Cys Arg Gln Ser Leu His Cys
                85                  90                  95

Asn Leu Ala Leu Asp Val Val Ser Phe Ser Lys Gly His Phe Lys Leu
                100                 105                 110

Leu Asn Val Lys Val Glu Val Arg Asp Ile Asn Asp His Ser Pro His
            115                 120                 125

Phe Pro Ser Glu Ile Met His Val Glu Val Ser Glu Ser Ser Val
        130                 135                 140

Gly Thr Arg Ile Pro Leu Glu Ile Ala Ile Asp Glu Asp Val Gly Ser
145                 150                 155                 160

Asn Ser Ile Gln Asn Phe Gln Ile Ser Asn Asn Ser His Phe Ser Ile
                165                 170                 175

Asp Val Leu Thr Arg Ala Asp Gly Val Lys Tyr Ala Asp Leu Val Leu
            180                 185                 190

Met Arg Glu Leu Asp Arg Glu Ile Gln Pro Thr Tyr Ile Met Glu Leu
            195                 200                 205

Leu Ala Met Asp Gly Gly Val Pro Ser Leu Ser Gly Thr Ala Val Val
210                 215                 220

Asn Ile Arg Val Leu Asp Phe Asn Asp Asn Ser Pro Val Phe Glu Arg
225                 230                 235                 240

Ser Thr Ile Ala Val Asp Leu Val Glu Asp Ala Pro Leu Gly Tyr Leu
                245                 250                 255

Leu Leu Glu Leu His Ala Thr Asp Asp Asp Glu Gly Val Asn Gly Glu
                260                 265                 270

Ile Val Tyr Gly Phe Ser Thr Leu Ala Ser Gln Glu Val Arg Gln Leu
            275                 280                 285

Phe Lys Ile Asn Ser Arg Thr Gly Ser Val Thr Leu Glu Gly Gln Val
            290                 295                 300
```

-continued

```
Asp Phe Glu Thr Lys Gln Thr Tyr Glu Phe Glu Val Gln Ala Gln Asp
305                 310                 315                 320

Leu Gly Pro Asn Pro Leu Thr Ala Thr Cys Lys Val Thr Val His Ile
            325                 330                 335

Leu Asp Val Asn Asp Asn Thr Pro Ala Ile Thr Ile Thr Pro Leu Thr
            340                 345                 350

Thr Val Asn Ala Gly Val Ala Tyr Ile Pro Glu Thr Ala Thr Lys Glu
        355                 360                 365

Asn Phe Ile Ala Leu Ile Ser Thr Thr Asp Arg Ala Ser Gly Ser Asn
    370                 375                 380

Gly Gln Val Arg Cys Thr Leu Tyr Gly His Glu His Phe Lys Leu Gln
385                 390                 395                 400

Gln Ala Tyr Glu Asp Ser Tyr Met Ile Val Thr Thr Ser Thr Leu Asp
                405                 410                 415

Arg Glu Asn Ile Ala Ala Tyr Ser Leu Thr Val Val Ala Glu Asp Leu
            420                 425                 430

Gly Phe Pro Ser Leu Lys Thr Lys Lys Tyr Tyr Thr Val Lys Val Ser
        435                 440                 445

Asp Glu Asn Asp Asn Ala Pro Val Phe Ser Lys Pro Gln Tyr Glu Ala
    450                 455                 460

Ser Ile Leu Glu Asn Asn Ala Pro Gly Ser Tyr Ile Thr Thr Val Ile
465                 470                 475                 480

Ala Arg Asp Ser Asp Ser Asp Gln Asn Gly Lys Val Asn Tyr Arg Leu
                485                 490                 495

Val Asp Ala Lys Val Met Gly Gln Ser Leu Thr Thr Phe Val Ser Leu
            500                 505                 510

Asp Ala Asp Ser Gly Val Leu Arg Ala Val Arg Ser Leu Asp Tyr Glu
        515                 520                 525

Lys Leu Lys Gln Leu Asp Phe Glu Ile Glu Ala Ala Asp Asn Gly Ile
    530                 535                 540

Pro Gln Leu Ser Thr Arg Val Gln Leu Asn Leu Arg Ile Val Asp Gln
545                 550                 555                 560

Asn Asp Asn Cys Pro Val Ile Thr Asn Pro Leu Leu Asn Asn Gly Ser
                565                 570                 575

Gly Glu Val Leu Leu Pro Ile Ser Ala Pro Gln Asn Tyr Leu Val Phe
            580                 585                 590

Gln Leu Lys Ala Glu Asp Ser Asp Glu Gly His Asn Ser Gln Leu Phe
        595                 600                 605

Tyr Thr Ile Leu Arg Asp Pro Ser Arg Leu Phe Ala Ile Asn Lys Glu
    610                 615                 620

Ser Gly Glu Val Phe Leu Lys Lys Gln Leu Asn Ser Asp His Ser Glu
625                 630                 635                 640

Asp Leu Ser Ile Val Val Ala Val Tyr Asp Leu Gly Arg Pro Ser Leu
                645                 650                 655

Ser Thr Asn Ala Thr Val Lys Phe Ile Leu Thr Asp Ser Phe Pro Ser
            660                 665                 670

Asn Val Glu Val Val Ile Leu Gln Pro Ser Ala Glu Glu Gln His Gln
        675                 680                 685

Ile Asp Met Ser Ile Ile Phe Ile Ala Val Leu Ala Gly Gly Cys Ala
    690                 695                 700

Leu Leu Leu Leu Ala Ile Phe Phe Val Ala Cys Thr Cys Lys Lys Lys
705                 710                 715                 720

Ala Gly Glu Phe Lys Gln Val Pro Glu Gln His Gly Thr Cys Asn Glu
```

```
                    725                 730                 735
Glu Arg Leu Leu Ser Thr Pro Ser Pro Gln Ser Val Ser Ser Leu
                740                 745                 750

Ser Gln Ser Glu Ser Cys Gln Leu Ser Ile Asn Thr Glu Ser Glu Asn
                755                 760                 765

Cys Ser Val Ser Ser Asn Gln Glu Gln His Gln Gln Thr Gly Ile Lys
            770                 775                 780

His Ser Ile Ser Val Pro Ser Tyr His Thr Ser Gly Trp His Leu Asp
785                 790                 795                 800

Asn Cys Ala Met Ser Ile Ser Gly His Ser His Met Gly His Ile Ser
                805                 810                 815

Thr Lys Asp Ser Gly Lys Gly Asp Ser Asp Phe Asn Asp Ser Asp Ser
            820                 825                 830

Asp Thr Ser Gly Glu Ser Gln Lys Lys Ser Ile Glu Gln Pro Met Gln
        835                 840                 845

Ala Gln Ala Ser Ala Gln Tyr Thr Asp Glu Ser Ala Gly Phe Arg His
850                 855                 860

Ala Asp Asn Tyr Phe Ser His Arg Ile Asn Lys Gly Pro Glu Asn Gly
865                 870                 875                 880

Asn Cys Thr Leu Gln Tyr Glu Lys Gly Tyr Arg Leu Ser Tyr Ser Val
                885                 890                 895

Ala Pro Ala His Tyr Asn Thr Tyr His Ala Arg Met Pro Asn Leu His
            900                 905                 910

Ile Pro Asn His Thr Leu Arg Asp Pro Tyr Tyr His Ile Asn Asn Pro
            915                 920                 925

Val Ala Asn Arg Met His Ala Glu Tyr Glu Arg Asp Leu Val Asn Arg
        930                 935                 940

Ser Ala Thr Leu Ser Pro Gln Arg Ser Ser Arg Tyr Gln Glu Phe
945                 950                 955                 960

Asn Tyr Ser Pro Gln Ile Ser Arg Gln Leu His Pro Ser Glu Ile Ala
                965                 970                 975

Thr Thr Phe (2) INFORMATION FOR SEQ ID NO:6:

(i) SEQUENCE CHARACTERISTICS:
        (A) LENGTH: 3655 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

GAATTCCCAG AGATGAACTC CTTGAGATTG TTTTAAATGA CTGCAGGTCT GGAAGGATTC      60

ACATTGCCAC ACTGTTTCTA GGCATGAAAA AACTGCAAGT TTCAACTTTG TTTTTGGTGC     120

AACTTTGATT CTTCAAGATG CTGCTTCTCT TCAGAGCCAT TCCAATGCTG CTGTTGGGAC     180

TGATGGTTTT ACAAACAGAC TGTGAAATTG CCCAGTACTA CATAGATGAA GAAGAACCCC     240

CTGGCACTGT AATTGCAGTG TTGTCACAAC ACTCCATATT TAACACTACA GATATACCTG     300

CAACCAATTT CCGTCTAATG AAGCAATTTA ATAATTCCCT TATCGGAGTC CGTGAGAGTG     360

ATGGGCAGCT GAGCATCATG GAGAGGATTG ACCGGGAGCA AATCTGCAGG CAGTCCCTTC     420

ACTGCAACCT GGCTTTGGAT GTGGTCAGCT TTTCCAAAGG ACACTTCAAG CTTCTGAACG     480

TGAAAGTGGA GGTGAGAGAC ATTAATGACC ATAGCCCTCA CTTTCCCAGT GAAATAATGC     540
```

| | |
|---|---|
| ATGTGGAGGT GTCTGAAAGT TCCTCTGTGG GCACCAGGAT TCCTTTAGAA ATTGCAATAG | 600 |
| ATGAAGATGT TGGGTCCAAC TCCATCCAGA ACTTTCAGAT CTCAAATAAT AGCCACTTCA | 660 |
| GCATTGATGT GCTAACCAGA GCAGATGGGG TGAAATATGC AGATTTAGTC TTAATGAGAG | 720 |
| AACTGGACAG GGAAATCCAG CCAACATACA TAATGGAGCT ACTAGCAATG GATGGGGGTG | 780 |
| TACCATCACT ATCTGGTACT GCAGTGGTTA ACATCCGAGT CCTGGACTTT AATGATAACA | 840 |
| GCCCAGTGTT TGAGAGAAGC ACCATTGCTG TGGACCTAGT AGAGGATGCT CCTCTGGGAT | 900 |
| ACCTTTTGTT GGAGTTACAT GCTACTGACG ATGATGAAGG AGTGAATGGA GAAATTGTTT | 960 |
| ATGGATTCAG CACTTTGGCA TCTCAAGAGG TACGTCAGCT ATTTAAAATT AACTCCAGAA | 1020 |
| CTGGCAGTGT TACTCTTGAA GGCCAAGTTG ATTTTGAGAC CAAGCAGACT TACGAATTTG | 1080 |
| AGGTACAAGC CCAAGATTTG GGCCCCAACC CACTGACTGC TACTTGTAAA GTAACTGTTC | 1140 |
| ATATACTTGA TGTAAATGAT AATACCCCAG CCATCACTAT TACCCCTCTG ACTACTGTAA | 1200 |
| ATGCAGGAGT TGCCTATATT CCAGAAACAG CCACAAAGGA GAACTTTATA GCTCTGATCA | 1260 |
| GCACTACTGA CAGAGCCTCT GGATCTAATG GACAAGTTCG CTGTACTCTT TATGGACATG | 1320 |
| AGCACTTTAA ACTACAGCAA GCTTATGAGG ACAGTTACAT GATAGTTACC ACCTCTACTT | 1380 |
| TAGACAGGGA AAACATAGCA GCGTACTCTT TGACAGTAGT TGCAGAAGAC CTTGGCTTCC | 1440 |
| CCTCATTGAA GACCAAAAAG TACTACACAG TCAAGGTTAG TGATGAGAAT GACAATGCAC | 1500 |
| CTGTATTTTC TAAACCCCAG TATGAAGCTT CTATTCTGGA AAATAATGCT CCAGGCTCTT | 1560 |
| ATATAACTAC AGTGATAGCC AGAGACTCTG ATAGTGATCA AAATGGCAAA GTAAATTACA | 1620 |
| GACTTGTGGA TGCAAAAGTG ATGGGCCAGT CACTAACAAC ATTTGTTTCT CTTGATGCGG | 1680 |
| ACTCTGGAGT ATTGAGAGCT GTTAGGTCTT TAGACTATGA AAAACTTAAA CAACTGGATT | 1740 |
| TTGAAATTGA AGCTGCAGAC AATGGGATCC CTCAACTCTC CACTCGCGTT CAACTAAATC | 1800 |
| TCAGAATAGT TGATCAAAAT GATAATTGCC CTGTGATAAC TAATCCTCTT CTTAATAATG | 1860 |
| GCTCGGGTGA AGTTCTGCTT CCCATCAGCG CTCCTCAAAA CTATTTAGTT TTCCAGCTCA | 1920 |
| AAGCCGAGGA TTCAGATGAA GGGCACAACT CCCAGCTGTT CTATACCATA CTGAGAGATC | 1980 |
| CAAGCAGATT GTTTGCCATT AACAAAGAAA GTGGTGAAGT GTTCCTGAAA AAACAATTAA | 2040 |
| ACTCTGACCA TTCAGAGGAC TTGAGCATAG TAGTTGCAGT GTATGACTTG GGAAGACCTT | 2100 |
| CATTATCCAC CAATGCTACA GTTAAATTCA TCCTCACCGA CTCTTTTCCT TCTAACGTTG | 2160 |
| AAGTCGTTAT TTTGCAACCA TCTGCAGAAG AGCAGCACCA GATCGATATG TCCATTATAT | 2220 |
| TCATTGCAGT GCTGGCTGGT GGTTGTGCTT TGCTACTTTT GGCCATCTTT TTTGTGGCCT | 2280 |
| GTACTTGTAA AAAGAAAGCT GGTGAATTTA AGCAGGTACC TGAACAACAT GGAACATGCA | 2340 |
| ATGAAGAACG CCTGTTAAGC ACCCCATCTC CCCAGTCGGT CTCTTCTTCT TTGTCTCAGT | 2400 |
| CTGAGTCATG CCAACTCTCC ATCAATACTG AATCTGAGAA TTGCAGCGTG TCCTCTAACC | 2460 |
| AAGAGCAGCA TCAGCAAACA GGCATAAAGC ACTCCATCTC TGTACCATCT TATCACACAT | 2520 |
| CTGGTTGGCA CCTGGACAAT TGTGCAATGA GCATAAGTGG ACATTCTCAC ATGGGGCACA | 2580 |
| TTAGTACAAA GGACAGTGGC AAAGGAGATA GTGACTTCAA TGACAGTGAC TCTGATACTA | 2640 |
| GTGGAGAATC ACAAAAGAAG AGCATTGAGC AGCCAATGCA GGCACAAGCC AGTGCTAAT | 2700 |
| ACACAGATGA ATCAGCAGGG TTCCGACATG CCGATAACTA TTTCAGCCAC CGAATCAACA | 2760 |
| AGGGTCCAGA AAATGGGAAC TGCACATTGC AATATGAAAA GGGCTATAGA CTGTCTTACT | 2820 |
| CTGTAGCTCC TGCTCATTAC AATACCTACC ATGCAAGAAT GCCTAACCTG CACATACCGA | 2880 |

```
ACCATACCCT TAGAGACCCT TATTACCATA TCAATAATCC TGTTGCTAAT CGGATGCACG    2940

CGGAATATGA AAGAGATTTA GTCAACAGAA GTGCAACGTT ATCTCCGCAG AGATCGTCTA    3000

GCAGATACCA AGAATTCAAT TACAGTCCGC AGATATCAAG ACAGCTTCAT CCTTCAGAAA    3060

TTGCTACAAC CTTTTAATCA TTAGGCATGC AAGTGAGAAT GCACAAAGGC AAGTGCTTTA    3120

GCATGAAAGC TAAATATATG GAGTCTCCCC TTTCCCTCTG ATGGATGGGG GGAGACACAG    3180

GACAGTGCAT AAATATACAG CTGCTTTCTA TTTGCATTTC ACTTGGGAAT TTTTTGTTTT    3240

TTTTACATAT TTATTTTTCC TGAATTGAAT GTGACATTGT CCTGTCACCT AACTAGCAAT    3300

TAAATCCACA GACCTACAGT CAAATATTTG AGGGCCCCTG AAACAGCACA TCAGTCAGGA    3360

CCTAAAGTGG CCTTTTTACT TTTAGCAGCT CCTGGGTCTG CCCTCTGTGT TAATCAGCCC    3420

CTGGTCAAGT CCTGAGTAGG ATCATGGCGT TTTTATATGC ATCTCACCTA CTTTGGACGT    3480

GATTTACACA TAATAGGAAA CGCTTGGTTT CAGTGAAGTC TGTGTTGTAT ATATTCTGTT    3540

ATATACACGC ATTTTGTGTT TGTGTATATA TTTCAAGTCC ATTCAGATAT GTGTATATAG    3600

TGCAGACCTT GTAAATTAAA TATTCTGATA CTTTTTCCTC AATAAATATT TAAAT         3655
```

(2) INFORMATION FOR SEQ ID NO:7:

(i) SEQUENCE CHARACTERISTICS:
        (A) LENGTH: 323 amino acids
        (B) TYPE: amino acid
        (D) TOPOLOGY: linear (ii) MOLECULE TYPE: peptide (xi) SEQUENCE DESCRIPTION: SEQ ID NO:7:

```
Met Val Cys Cys Gly Pro Gly Arg Met Leu Leu Gly Trp Ala Gly Leu
1               5                  10                  15

Leu Val Leu Ala Ala Leu Cys Leu Gln Val Pro Gly Ala Gln Ala
            20                  25                  30

Ala Ala Cys Glu Pro Val Arg Ile Pro Leu Cys Lys Ser Leu Pro Trp
        35                  40                  45

Asn Met Thr Lys Met Pro Asn His Leu His His Ser Thr Gln Ala Asn
    50                  55                  60

Ala Ile Leu Ala Met Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
            100                 105                 110

Glu Arg Ala Arg Gln Gly Cys Glu Pro Ile Leu Ile Lys Tyr Arg His
        115                 120                 125

Ser Trp Pro Glu Ser Leu Ala Cys Asp Glu Leu Pro Val Tyr Asp Arg
    130                 135                 140

Gly Val Cys Ile Ser Pro Glu Ala Ile Val Thr Ala Asp Gly Ala Asp
145                 150                 155                 160

Phe Pro Met Asp Ser Ser Thr Gly His Cys Arg Gly Ala Ser Ser Glu
                165                 170                 175

Arg Cys Lys Cys Lys Pro Val Arg Ala Thr Gln Lys Thr Tyr Phe Arg
            180                 185                 190

Asn Asn Tyr Asn Tyr Val Ile Arg Ala Lys Val Lys Glu Val Lys Met
        195                 200                 205

Lys Cys His Asp Val Thr Ala Val Val Glu Val Lys Glu Ile Leu Lys
    210                 215                 220
```

```
Ala Ser Leu Val Asn Ile Pro Arg Asp Thr Val Asn Leu Tyr Thr Thr
225                 230                 235                 240

Ser Gly Cys Leu Cys Pro Pro Leu Thr Val Asn Glu Glu Tyr Val Ile
            245                 250                 255

Met Gly Tyr Glu Asp Glu Arg Ser Arg Leu Leu Leu Val Glu Gly
        260                 265                 270

Ser Ile Ala Glu Lys Trp Lys Asp Arg Leu Gly Lys Lys Val Lys Arg
        275                 280                 285

Trp Asp Met Lys Leu Arg His Leu Gly Leu Gly Lys Thr Asp Ala Ser
        290                 295                 300

Asp Ser Thr Gln Asn Gln Lys Ser Gly Arg Asn Ser Asn Pro Arg Pro
305                 310                 315                 320

Ala Arg Ser (2) INFORMATION FOR SEQ ID NO:8:

(i) SEQUENCE CHARACTERISTICS:
        (A) LENGTH: 2176 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:8:

AAGCCTGGGA CCATGGTCTG CTGCGGCCCG GGACGGATGC TGCTAGGATG GGCCGGGTTG      60

CTAGTCCTGG CTGCTCTCTG CCTGCTCCAG GTGCCCGGAG CTCAGGCTGC AGCCTGTGAG     120

CCTGTCCGCA TCCCGCTGTG CAAGTCCCTT CCCTGGAACA TGACCAAGAT GCCCAACCAC     180

CTGCACCACA GCACCCAGGC TAACGCCATC CTGGCCATGG AACAGTTCGA AGGGCTGCTG     240

GGCACCCACT GCAGCCCGGA TCTTCTCTTC TTCCTCTGTG CAATGTACGC ACCCATTTGC     300

ACCATCGACT TCCAGCACGA GCCCATCAAG CCCTGCAAGT CTGTGTGTGA GCGCGCCCGA     360

CAGGGCTGCG AGCCCATTCT CATCAAGTAC CGCCACTCGT GGCCGGAAAG CTTGGCCTGC     420

GACGAGCTGC CGGTGTACGA CCGCGGCGTG TGCATCTCTC CTGAGGCCAT CGTCACCGCG     480

GACGGAGCGG ATTTTCCTAT GGATTCAAGT ACTGGACACT GCAGAGGGGC AAGCAGCGAA     540

CGTTGCAAAT GTAAGCCTGT CAGAGCTACA CAGAAGACCT ATTTCCGGAA CAATTACAAC     600

TATGTCATCC GGGCTAAAGT TAAAGAGGTA AAGATGAAAT GTCATGATGT GACCGCCGTT     660

GTGGAAGTGA AGGAAATTCT AAAGGCATCA CTGGTAAACA TTCCAAGGGA CACCGTCAAT     720

CTTTATACCA CCTCTGGCTG CCTCTGTCCT CCACTTACTG TCAATGAGGA ATATGTCATC     780

ATGGGCTATG AAGACGAGGA ACGTTCCAGG TTACTCTTGG TAGAAGGCTC TATAGCTGAG     840

AAGTGGAAGG ATCGGCTTGG TAAGAAAGTC AAGCGCTGGG ATATGAAACT CCGACACCTT     900

GGACTGGGTA AAACTGATGC TAGCGATTCC ACTCAGAATC AGAAGTCTGG CAGGAACTCT     960

AATCCCCGGC CAGCACGCAG CTAAATCCTG AAATGTAAAA GGCCACACCC ACGGACTCCC    1020

TTCTAAGACT GGCGCTGGTG GACTAACAAA GGAAAACCGC ACAGTTGTGC TCGTGACCGA    1080

TTGTTTACCG CAGACACCGC GTGGCTACCG AAGTTACTTC CGGTCCCCTT TCTCCTGCTT    1140

CTTAATGGCG TGGGGTTAGA TCCTTTAATA TGTTATATAT TCTGTTTCAT CAATCACGTG    1200

GGGACTGTTC TTTTGCAACC AGAATAGTAA ATTAAATATG TTGATGCTAA GGTTTCTGTA    1260

CTGGACTCCC TGGGTTTAAT TTGGTGTTCT GTACCCTGAT TGAGAATGCA ATGTTTCATG    1320

TAAAGAGAGA ATCCTGGTCA TATCTCAAGA ACTAGATATT GCTGTAAGAC AGCCTCTGCT    1380
```

```
GCTGCGCTTA TAGTCTTGTG TTTGTATGCC TTTGTCCATT TCCCTCATGC TGTGAAAGTT    1440

ATACATGTTT ATAAAGGTAG AACGGCATTT TGAAATCAGA CACTGCACAA GCAGAGTAGC    1500

CCAACACCAG GAAGCATTTA TGAGGAAACG CCACACAGCA TGACTTATTT TCAAGATTGG    1560

CAGGCAGCAA AATAAATAGT GTTGGGAGCC AAGAAAAGAA TATTTTGCCT GGTTAAGGGG    1620

CACACTGGAA TCAGTAGCCC TTGAGCCATT AACAGCAGTG TTCTTCTGGC AAGTTTTTGA    1680

TTTGTTCATA AATGTATTCA CGAGCATTAG AGATGAACTT ATAACTAGAC ATCTGTTGTT    1740

ATCTCTATAG CTCTGCTTCC TTCTAAATCA AACCCATTGT TGGATGCTCC CTCTCCATTC    1800

ATAAATAAAT TTGGCTTGCT GTATTGGCCA GGAAAAGAAA GTATTAAAGT ATGCATGCAT    1860

GTGCACCAGG GTGTTATTTA ACAGAGGTAT GTAACTCTAT AAAAGACTAT AATTTACAGG    1920

ACACGGAAAT GTGCACATTT GTTTACTTTT TTTCTTCCTT TTGCTTTGGG CTTGTGATTT    1980

TGGTTTTTGG TGTGTTTATG TCTGTATTTT GGGGGGTGGG TAGGTTTAAG CCATTGCACA    2040

TTCAAGTTGA ACTAGATTAG AGTAGACTAG GCTCATTGGC CTAGACATTA TGATTTGAAT    2100

TTGTGTTGTT TAATGCTCCA TCAAGATGTC TAATAAAAGG AATATGGTTG TCAACAGAGA    2160

CGACAACAAC AACAAA                                                   2176
```

(2) INFORMATION FOR SEQ ID NO:9:

(i) SEQUENCE CHARACTERISTICS:
        (A) LENGTH: 325 amino acids
        (B) TYPE: amino acid
        (D) TOPOLOGY: linear (ii) MOLECULE TYPE: peptide (xi) SEQUENCE DESCRIPTION: SEQ ID NO:9:

```
Met Val Cys Gly Ser Pro Gly Gly Met Leu Leu Leu Arg Ala Gly Leu
1               5                   10                  15

Leu Ala Leu Ala Ala Leu Cys Leu Leu Arg Val Pro Gly Ala Arg Ala
                20                  25                  30

Ala Ala Cys Glu Pro Val Arg Ile Pro Leu Cys Lys Ser Leu Pro Trp
            35                  40                  45

Asn Met Thr Lys Met Pro Asn His Leu His His Ser Thr Gln Ala Asn
    50                  55                  60

Ala Ile Leu Ala Ile Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
                100                 105                 110

Glu Arg Ala Arg Gln Gly Cys Glu Pro Ile Leu Ile Lys Tyr Arg His
            115                 120                 125

Ser Trp Pro Glu Asn Leu Ala Cys Glu Glu Leu Pro Val Tyr Asp Arg
    130                 135                 140

Gly Val Cys Ile Ser Pro Glu Ala Ile Val Thr Ala Asp Gly Ala Asp
145                 150                 155                 160

Phe Pro Met Asp Ser Ser Asn Gly Asn Cys Arg Gly Ala Ser Ser Glu
                165                 170                 175

Arg Cys Lys Cys Lys Pro Ile Arg Ala Thr Gln Lys Thr Tyr Phe Arg
            180                 185                 190

Asn Asn Tyr Asn Tyr Val Ile Arg Ala Lys Val Lys Glu Ile Lys Thr
    195                 200                 205
```

```
Lys Cys His Asp Val Thr Ala Val Val Glu Val Lys Glu Ile Leu Lys
    210                 215                 220

Ser Ser Leu Val Asn Ile Pro Arg Asp Thr Val Asn Leu Tyr Thr Ser
225                 230                 235                 240

Ser Gly Cys Leu Cys Pro Pro Leu Asn Val Asn Glu Glu Tyr Ile Ile
                245                 250                 255

Met Gly Tyr Glu Asp Glu Arg Ser Arg Leu Leu Leu Val Glu Gly
            260                 265                 270

Ser Ile Ala Glu Lys Trp Lys Asp Arg Leu Gly Lys Lys Val Lys Arg
            275                 280                 285

Trp Asp Met Lys Leu Arg His Leu Gly Leu Ser Lys Ser Asp Ser Ser
    290                 295                 300

Asn Ser Asp Ser Thr Gln Ser Gln Lys Ser Gly Arg Asn Ser Asn Pro
305                 310                 315                 320

Arg Gln Ala Arg Asn
            325

(2) INFORMATION FOR SEQ ID NO:10:

(i) SEQUENCE CHARACTERISTICS:
        (A) LENGTH: 1893 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

GGCGGAGCGG GCCTTTTGGC GTCCACTGCG CGGCTGCACC CTGCCCCATC TGCCGGGATC      60

ATGGTCTGCG GCAGCCCGGG AGGGATGCTG CTGCTGCGGG CCGGGCTGCT TGCCCTGGCT     120

GCTCTCTGCC TGCTCCGGGT GCCCGGGGCT CGGGCTGCAG CCTGTGAGCC CGTCCGCATC     180

CCCCTGTGCA AGTCCCTGCC CTGGAACATG ACTAAGATGC CAACCACCT GCACCACAGC      240

ACTCAGGCCA ACGCCATCCT GGCCATCGAG CAGTTCGAAG GTCTGCTGGG CACCCACTGC     300

AGCCCCGATC TGCTCTTCTT CCTCTGTGCC ATGTACGCGC CCATCTGCAC CATTGACTTC     360

CAGCACGAGC CCATCAAGCC CTGTAAGTCT GTGTGCGAGC GGGCCCGGCA GGGCTGTGAG     420

CCCATACTCA TCAAGTACCG CCACTCGTGG CCGGAGAACC TGGCCTGCGA GGAGCTGCCA     480

GTGTACGACA GGGGCGTGTG CATCTCTCCC GAGGCCATCG TTACTGCGGA CGGAGCTGAT     540

TTTCCTATGG ATTCTAGTAA CGGAAACTGT AGAGGGCAA GCAGTGAACG CTGTAAATGT      600

AAGCCTATTA GAGCTACACA GAAGACCTAT TTCCGGAACA ATTACAACTA TGTCATTCGG     660

GCTAAAGTTA AGAGATAAA GACTAAGTGC CATGATGTGA CTGCAGTAGT GGAGGTGAAG      720

GAGATTCTAA AGTCCTCTCT GGTAAACATT CCACGGGACA CTGTCAACCT CTATACCAGC     780

TCTGGCTGCC TCTGCCCTCC ACTTAATGTT AATGAGGAAT ATATCATCAT GGGCTATGAA     840

GATGAGGAAC GTTCCAGATT ACTCTTGGTG GAAGGCTCTA TAGCTGAGAA GTGGAAGGAT     900

CGACTCGGTA AAAAAGTTAA GCGCTGGGAT ATGAAGCTTC GTCATCTTGG ACTCAGTAAA     960

AGTGATTCTA GCAATAGTGA TTCCACTCAG AGTCAGAAGT CTGGCAGGAA CTCGAACCCC    1020

CGGCAAGCAC GCAACTAAAT CCCGAAATAC AAAAAGTAAC ACAGTGGACT TCCTATTAAG    1080

ACTTACTTGC ATTGCTGGAC TAGCAAAGGA AAATTGCACT ATTGCACATC ATATTCTATT    1140

GTTTACTATA AAAATCATGT GATAACTGAT TATTACTTCT GTTTCTCTTT TGGTTTCTGC    1200

TTCTCTCTTC TCTCAACCCC TTTGTAATGG TTTGGGGGCA GACTCTTAAG TATATTGTGA    1260
```

-continued

```
GTTTTCTATT TCACTAATCA TGAGAAAAAC TGTTCTTTTG CAATAATAAT AAATTAAACA    1320

TGCTGTTACC AGAGCCTCTT TGCTGAGTCT CCAGATGTTA ATTTACTTTC TGCACCCCAA    1380

TTGGGAATGC AATATTGGAT GAAAAGAGAG GTTTCTGGTA TTCACAGAAA GCTAGATATG    1440

CCTTAAAACA TACTCTGCCG ATCTAATTAC AGCCTTATTT TTGTATGCCT TTTGGGCATT    1500

CTCCTCATGC TTAGAAAGTT CCAAATGTTT ATAAAGGTAA AATGGCAGTT TGAAGTCAAA    1560

TGTCACATAG GCAAAGCAAT CAAGCACCAG GAAGTGTTTA TGAGGAAACA ACACCCAAGA    1620

TGAATTATTT TTGAGACTGT CAGGAAGTAA AATAAATAGG AGCTTAAGAA AGAACATTTT    1680

GCCTGATTGA GAAGCACAAC TGAAACCAGT AGCCGCTGGG GTGTTAATGG TAGCATTCTT    1740

CTTTTGGCAA TACATTTGAT TTGTTCATGA ATATATTAAT CAGCATTAGA GAATGAATT     1800

ATAACTAGAC ATCTGCTGTT ATCACCATAG TTTTGTTTAA TTTGCTTCCT TTTAAATAAA    1860

CCCATTGGTG AAAGTCAAAA AAAAAAAAAA AAA                                 1893
```

ENDODERM, CARDIAC AND NEURAL INDUCING FACTORS

This application claims the benefit of U.S. Provisional application Ser. No. 60/020,150 filed Jun. 20, 1996.

This invention was made with Government support under grant contract number HD-21502, awarded by the National Institutes of Health. The Government has certain rights in this invention.

FIELD OF THE INVENTION

The invention generally relates to growth factors, neurotrophic factors, and their inhibitors, and more particularly to several new growth factors with neural, endodermal, and cardiac tissue inducing activity, to complexes and compositions including the factors, and to DNA or RNA coding sequences for the factors. Further, one of the novel growth factors should be useful in tumor suppression gene therapy.

BACKGROUND OF THE INVENTION

Growth factors are substances, such as polypeptide hormones, which affect the growth of defined populations of animal cells in vivo or in vitro, but which are not nutrient substances. Proteins involved in the growth and differentiation of tissues may promote or inhibit growth, and promote or inhibit differentiation, and thus the general term "growth factor" includes cytokines, trophic factors, and their inhibitors.

Widespread neuronal cell death accompanies normal development of the central and peripheral nervous systems. Studies of peripheral target tissues during development have shown that neuronal cell death results from the competition among neurons for limiting amounts of survivor factors ("neurotrophic factors"). The earliest identified of these, nerve growth factor ("NGF"), is the most fully characterized and has been shown to be essential for the survival of sympathetic and neural crest-derived sensory neurons during early development of both chick and rat.

One family of neurotropic factors are the Wnts, which have dorsal axis-inducing activity. Most of the Wnt proteins are bound to cell surfaces. (See, e.g., Sokol et al., *Science*, 249, pp. 561–564, 1990.) Dorsal axis-inducing activity in Xenopus embryos by one member of this family (Xwnt-8) was described by Smith and Harland in 1991, *Cell*, 67, pp. 753–765. The authors described using RNA injections as a strategy for identifying endogenous RNAs involved in dorsal patterning to rescue dorsal development in embryos that were ventralized by UV irradiation.

Another member of the growth and neurotropic factor family was subsequently discovered and described by Harland and Smith, which they termed "noggin." (*Cell*, 70, pp. 829–840 (1992).) Noggin is a good candidate to function as a signaling molecule in Nieuwkoop's center, by virtue of its maternal transcripts, and in Spemann's organizer, through its zygotic organizer-specific expression. Besides noggin, other secreted factors may be involved in the organizer phenomenon.

Another Xenopus gene designated "chordin" that begins to be expressed in Spemann's organizer and that can completely rescue axial development in ventralized embryos was described by Sasai et al., *Cell*, 79, pp. 779–790, 1994. In addition to dorsalizing mesoderm, chordin has the ability to induce neural tissue and its activities are antagonized by Bone Morphogenetic Protein-4 (Sasai et al., *Nature*, 376, pp. 333–336, 1995).

Therefore, the dorsal lip or Spemann's organizer of the Xenopus embryo is an ideal tissue for seeking novel growth and neurotrophic factors. New growth and neurotrophic factors are useful agents, particularly those that are secreted due to their ability to be used in physiologically active, soluble forms because these factors, their receptors, and DNA or RNA coding sequences therefore and fragments thereof are useful in a number of therapeutic, clinical, research, diagnostic, and drug design applications.

SUMMARY OF THE INVENTION

In one aspect of the present invention, the sequence of the novel peptide that can be in substantially purified form is shown by SEQ ID NO:1. The Xenopus derived SEQ ID NO:1 has been designated "cerberus," and this peptide is capable of inducing endodermal, cardiac, and neural tissue development in vertebrates when expressed. The nucleotide sequence which, when expressed results in cerberus, is illustrated by SEQ ID NO:2. Since peptides of the invention induce endodermal, cardiac, and neural tissue differentiation in vertebrates, they should be able to be prepared in physiologically active form for a number of therapeutic, clinical, and diagnostic applications.

Cerberus was isolated during a search for molecules expressed specifically in Spemann's organizer containing a secretory signal sequence. In addition to cerberus, two other novel cDNAs were identified.

The Xenopus derived peptide that can be deduced from SEQ ID NO:3 encodes a novel protein we had earlier designated as "frazzled," a secreted protein of 318 amino acids that has dorsalizing activity in Xenopus embryos. We now designate the novel protein as "frzb-1." The gene for frzb-1 is expressed in many adult tissues of many animals, three of the cDNAs (Xenopus, mouse, and human) have been cloned by us. The accession numbers for the Xenopus, mouse, and human frzb-1 cDNA sequences of the gene now designated frzb-1 are U68059, U68058, and U68057, respectively. Frzb-1 has some degree of sequence similarity to the Drosophila gene frizzled which has been shown to encode a seven-transmembrane protein that can act both as a signalling and as a receptor protein (Vinson et al., *Nature*, 338, pp. 263–264, 1989; Vinson and Adler, *Nature*, 329, pp. 549–551, 1987). Vertebrate homologues of Frizzled have been isolated and they too were found to be anchored to the cell membrane by seven membrane spanning domains (Wang et al., *J. Biol. Chem.*, 271, pp. 4468–4476, 1996). Frzb-1 differs from the frizzled proteins in that it is an entirely soluble, diffusible secreted protein and therefore suitable as a therapeutic agent. The nucleotide sequence derived from Xenopus that, when expressed, results in frzb-1 protein is illustrated by SEQ ID NO:4. The frzb-1 protein derived from mouse is shown as SEQ ID NO:7, while the mouse frzb-1 nucleotide sequence is SEQ ID NO:8. The human derived frzb-1 protein is illustrated by SEQ ID NO:9, and the human frzb-1 nucleotide sequence is SEQ ID NO:10.

Frzb-1 is an antagonist of Wnts in vivo, and thus is believed to find utility as a tumor suppressor gene, since overexpressed Wnt proteins cause cancer. Frzb-1 may also be a useful vehicle for solubilization and therapeutic delivery of Wnt proteins complexed with it.

The final cDNA isolated containing a signal sequence results in a peptide designated Paraxial protocadherin (PAPC). The cDNA for PAPC is a divergent member of the cadherin multigene family. PAPC is most related to protocadherin 43 reported by Sano et al., *The EMBO J.*, 12, pp. 2249–2256, 1993. As shown in SEQ ID NO:5, the PAPC gene encodes a transmembrane protein of 896 amino acids, of which 187 are part of an intracellular domain. PAPC is a cell adhesion molecule, and microinjection of PAPC mRNA constructs into Xenopus embryos suggest that PAPC acts as a molecule involved in mesoderm differentiation. A soluble form of the PAPC extracellular domain is able to block muscle and mesoderm formation in Xenopus embryos. The nucleotide sequence encoding Xenopus PAPC is provided in SEQ ID NO:6.

Cerberus, frzb-1, or PAPC or fragments thereof (which also may be synthesized by in vitro methods) may be fused (by recombinant expression or in vitro covalent methods) to an immunogenic polypeptide and this, in turn, may be used to immunize an animal in order to raise antibodies against the novel proteins. Antibodies are recoverable from the serum of immunized animals. Alternatively, monoclonal antibodies may be prepared from cells from the immunized animal in conventional fashion. Immobilized antibodies are useful particularly in the diagnosis (in vitro or in vivo) or purification of cerberus, frzb-1, or PAPC.

Substitutional, deletional, or insertional mutants of the novel polypeptides may be prepared by in vitro or recombinant methods and screened for immuno-crossreactivity with cerberus, frzb-1, or PAPC and for cerberus antagonist or agonist activity.

Cerberus or frzb-1 also may be derivatized in vitro in order to prepare immobilized and labelled proteins, particularly for purposes of diagnosis of insufficiencies thereof, or for affinity purification of antibodies thereto.

Among applications for the novel proteins are tissue replacement therapy and, because frzb-1 is an antagonist of Wnt signaling, tumor suppression therapies. The cerberus receptor may define a novel signalling pathway. In addition, frzb-1 could permit the isolation of novel members of the Wnt family of growth factors.

BRIEF DESCRIPTION OF THE DRAWINGS

FIG. 1 illustrates the amino acid sequence (SEQ ID NO:1) of the FIG. 2 cDNA clone for cerberus;

FIG. 2 illustrates a cDNA clone (SEQ ID NO:2) for cerberus derived from Xenopus. Sense strand is on top (5' to 3' direction) and the antisense strand on the bottom line (in the opposite direction);

FIGS. 3 and 4 show the amino acid and nucleotide sequence, respectively, of full-length frzb-1 from Xenopus (SEQ ID NOS:3 and 4);

FIGS. 5 and 6 show the amino acid and nucleotide sequence, respectively, of full-length PAPC from Xenopus (SEQ ID NOS:5 and 6);

FIGS. 7 and 8 show the amino acid and nucleotide sequence, respectively, of full-length frzb-1 from mouse (SEQ ID NOS:7 and 8); and FIGS. 9 and 10 show the amino acid and nucleotide sequence, respectively, of full-length frzb-1 from human (SEQ ID NOS:9 and 10).

DETAILED DESCRIPTION OF THE PREFERRED EMBODIMENTS

Among the several novel proteins and their nucleotide sequences described herein, is a novel endodermal, cardiac, and neural inducing factor in vertebrates that we have named "cerberus." When referring to cerberus, the present invention also contemplates the use of fragments, derivatives, agonists, or antagonists of cerberus molecules. Because cerberus has no homology to any reported growth factors, it is proposed to be the founding member of a novel family of growth factors with potent biological activities, which may be isolated using SEQ ID NO:2.

The amphibian organizer consists of several cell populations with region-specific inducing activities. On the basis of morphogenetic movements, three very different cell populations can be distinguished in the organizer. First, cells with crawling migration movements involute, fanning out to form the prechordal plate. Second, cells involute through the dorsal lip driven by convergence and extension movements, giving rise to the notochord of the trunk. Third, involution ceases and the continuation of mediolateral intercalation movements leads to posterior extension movements and to the formation of the tail notochord and of the chordoneural hinge. The three cell populations correspond to the head, trunk, and tail organizers, respectively.

The cerberus gene is expressed at the right time and place to participate in cell signalling by Spemann's organizer. Specifically, cerberus is expressed in the head organizing region that consists of crawling-migrating cells. The cerberus expressing region corresponds to the prospective foregut, including the liver and pancreas anlage, and the heart mesoderm. Cerberus expression is activated by chordin, noggin, and organizer-specific homeobox genes.

Our studies were conducted in early embryos of the frog *Xenopus laevis*. The frog embryo is well suited to experiments, particularly experiments pertaining to generating and maintaining regional differences within the embryo for determining roles in tissue differentiation. It is easy to culture embryos with access to the embryos even at very early stages of development (preceding and during the formation of body pattern and differentiation) and the embryos are large. The initial work with noggin and chordin also had been in Xenopus embryos, and, as predicted, was highly conserved among vertebrates. Predictions based on work with Xenopus as to corresponding human noggin were proven true and the ability to clone the gene for human noggin was readily accomplished. (See the description of xenopus work and cloning information in PCT application, published Mar. 17, 1994, WO 9 405 800, and the subsequent human cloning based thereon in the PCT application, also published Mar. 17, 1994, as WO 9 405 791.)

Cloning

The cloning of cerberus, frzb-1, and PAPC resulted from a comprehensive screen for cDNAs enriched in Spemann's organizer. Subtractive differential screening was performed as follows. In brief, poly $A^+$ RNA was isolated from 300 dorsal lip and ventral marginal zone (VMZ) explants at stage 10½. After first strand cDNA synthesis approximately 70–80% of common sequences were removed by substraction with biotinylated VMZ poly $A^+$ RNA prepared from 1500 ventral gastrula halves. For differential screening, duplicate filters (2000 plaques per 15 cm plate, a total of 80,000 clones screened) of an unamplified oriented dorsal lip library were hybridized with radiolabeled dorsal lip or VMZ cDNA. Putative organizer-specific clones were isolated, grouped by sequence analysis from the 5' end and whole-mount in situ hybridization, and subsequently classified into known and new dorsal-specific genes. Rescreening of the library (100,000 independent phages) with a cerberus probe resulted in the isolation of 45 additional clones, 31 of which had similar size as the longest one of the 11 original clones indicating that they were presumably full-length cDNAs. The longest cDNAs for cerberus, frzb-1, and PAPC were completely sequenced.

To explore the molecular complexity of Spemann's organizer we performed a comprehensive differential screen for dorsal-specific cDNAs. The method was designed to identify abundant cDNAs without bias as to their function. As shown in Table 1, five previously known cDNAs and five new ones were isolated, of which three (expressed as cerberus, frzb-1, and PAPC, respectively) had secretory signal sequences.

TABLE 1

| | Gene Product | No. of Isolates |
|---|---|---|
| Previously Known Genes | | |
| Chordin | novel secreted protein | 70 |
| Goosecoid | homeobox gene | 3 |
| Pintallavis/XFKH-1 | forkhead/transcription factor | 2 |
| Xnot-2 | homeobox gene | 1 |
| Xlim-1 | homeobox gene | 1 |
| New Genes | | |
| Cerberus | novel secreted protein | 11 |
| PAPC | cadherin-like/transmembrane | 2 |
| Frzb-1 | novel secreted protein | 1 |
| Sox-2 | sry/transcription factor | 1 |
| Fkh-like | forkhead/transcription factor | 1 |

The most abundant dorsal-specific cDNA was chordin (chd), with 70 independent isolates. The second most abundant cDNA was isolated 11 times and named cerberus (after a mythological guardian dog with multiple heads). The cerberus cDNA encodes a putative secreted polypeptide of 270 amino acids, with an amino terminal hydrophobic signal sequence and a carboxy terminal cysteine-rich region (FIG. 1). Cerberus is expressed specifically in the head organizer region of the Xenopus embryo, including the future foregut.

An abundant mRNA found in the dorsal region of the *Xenopus gastrula* encodes the novel putative secreted protein we have designated as cerberus. Cerberus mRNA has potent inducing activity in Xenopus embryos, leading to the formation of ectopic heads. Unlike other organizer-specific factors, cerberus does not dorsalize mesoderm and is instead an inhibitor of trunk-tail mesoderm. Cerberus is expressed in the anterior-most domain of the gastrula including the leading edge of the deep layer of the dorsal lip a region that, as shown here, gives rise to foregut and midgut endoderm. Cerberus promotes the formation of cement gland, olfactory placodes, cyclopic eyes, forebrain, and duplicated heart and liver (a foregut derivative). Because the pancreas is also derived from this foregut region, it is likely that cerberus induces pancreas in addition to liver. The expression pattern and inducing activities of cerberus suggest a role for a previously neglected region of the embryo, the prospective foregut endoderm, in the induction of the anterior head region of the embryo.

Turning to FIG. 1, *Xenopus cerberus* encodes a putative secreted protein transiently expressed during embryogenesis and the deduced amino acid sequence of *Xenopus cerberus* is shown. The signal peptide sequence and the nine cysteine residues in the carboxy-terminus are indicated in bold. Potential N-linked glycosylation sites are underlined. In database searches the cerberus protein showed limited similarity only to the mammalian Dan protein, a possible tumor suppressor proposed to be a DNA-binding protein.

Cerberus appears to be a pioneer protein, as its amino acid sequence and the spacing of its 9 cysteine residues were not significantly similar to other proteins in the databases (NCBI-Gen Bank release 93.0). We conclude that the second most abundant dorsal-specific cDNA encodes a novel putative secreted factor, which should be the founding member of a novel family of growth factors active in cell differentiation.

Cerberus Demarcates an Anterior Organizer Domain

Cerberus mRNA is expressed at low levels in the unfertilized egg, and zygotic transcripts start accumulating at early gastrula. Expression continues during gastrula and early neurula, rapidly declining during neurulation. Importantly, cerberus expression starts about one hour after that of chd, suggesting that cerberus could act downstream of the chd signal.

Whole-mount in situ hybridizations reveal that expression starts in the yolky endomesodermal cells located in the deep layer of the organizer. The cerberus domain includes the leading edge of the most anterior organizer cells and extends into the lateral mesoderm. The leading edge gives rise to liver, pancreas, and foregut in its midline, and the more lateral region gives rise to heart mesoderm at later stages of development.

FIG. 2 sets out the sequence of a full length Xenopus cDNA for cerberus.

This entirely new molecule has demonstrated physiological properties that should prove useful in therapeutic, diagnostic, and clinical applications that require regeneration, differentiation, or repair of tissues, such wound repair, neuronal regenerational or transplantation, supplementation of heart muscle differentiation, differentiation of pancreas and liver, and other applications in which cell differentiation processes are to be induced.

The second, novel, secreted protein we have discovered is called "frzb-1," which was shown to be a secreted protein in Xenopus oocyte microinjection experiments. Thus it provides a natural soluble form of the related extracellular domains of Drosophila and vertebrate frizzled proteins. We propose that the latter proteins could be converted into active soluble forms by introducing a stop codon before the first transmembrane domain. We have noted that the cysteine-rich region of frzb-1 and frizzled contains some overall structural homology with Wnt proteins using the Profile Search homology program (Gribskov, *Meth. Enzymol.*, 183, pp. 146–159, 1990). This had raised the interesting possibility that frzb-1 could interact directly with Wnt growth factors in the extracellular space. This was because we had found that when microinjected into Xenopus embryos, frzb-1 constructs have moderate dorsalizing activity, leading to the formation of embryos with enlarged brain and head, and shortened truck. Somatic muscle differentiation, which requires Xwnt-8, was inhibited. In the case of frzb-1, an attractive hypothesis, suggested by the structural homologies, was that it may act as an inhibitor of Wnt-8, a growth factor that has ventralizing activity in the Xenopus embryo (Christian and Moon, *Genes Dev.*, 7, pp. 13–28, 1993). We have shown that frzb-1 can interact with Xwnt-8 and Wnt-1, and it is expected that it could also interact with other members of the Wnt family of growth factors, of which at least 15 members exist in mammals. In addition, a possible interaction with Wnts was suggested by the recent discovery that dishevelled, a gene acting downstream of wingless, has strong genetic interaction with frizzled mutants in Drosophila (Krasnow et al., *Development*, 121, pp. 4095–4102, 1995). This possibility has been explored in depth (Leyns et al., *Cell*, 88, pp. 747–756, Mar. 21, 1997), because a soluble antagonist of the Wnt family of proteins is expected to be of great therapeutic value. Examples 1 and 2 illustrate tests that show antagonism of Xwnt-8 by binding to frzb-1.

Vertebrate homologues of Frizzled have been isolated and they too are anchored to the cell membrane by seven membrane spanning domains (Wang et al., *J. Biol. Chem.*, 271, pp. 4468–4476, 1996). Frzb-1 differs from the frizzled proteins in that it is an entirely soluble, diffusible secreted protein and therefore suitable as a therapeutic agent. The nucleotide sequence that when expressed results in frzb-1 protein is illustrated by SEQ ID NO:4.

SEQ ID NO:4 corresponds to the Xenopus homolog, but by using it in BLAST searches (and by cloning mouse frzb-1) we had been able to assemble the sequence of the entire mature human frzb-1 protein, SEQ ID NO:9. Indeed, human frzb-1 is encoded in six expressed sequence tags (ESTs) available in Genebank. The human frzb-1 sequence can be assembled by overlapping in the 5' to 3' direction the ESTs with the following accession numbers in Genebank: H18848, R63748, W38677, W44760, H38379, and N71244. No function had yet been assigned to these EST sequences, but we believe and thus propose here that human frzb-1 will have similar functions in cell differentiation to those described above for Xenopus frzb-1. The nucleotide sequence of human frzb-1 is shown in SEQ ID NO:10. The mouse frzb-1 protein and nucleotide sequences are provided by SEQ ID NOS:7 and 8, respectively.

In particular, we believe that frzb-1 will prove useful in gene therapy of human cancer cells. In this rapidly developing field, one approach is to introduce vectors expressing anti-sense sequences to block expression of dominant ocogenes and growth factor receptors. Another approach is to produce episomal vectors that will replicate in human cells in a controlled fashion without transforming the cells. For an example of the latter (an episomal expression vector system for human gene therapy), reference is made to U.S. Pat. No. 5,624,820, issued Apr. 29, 1997, inventor Cooper.

Gene therapy now includes uses of human tumor suppression genes. For example, U.S. Pat. No. 5,491,064, issued Feb. 13, 1996, discloses a tumor suppression gene localized on chromosome 11 and described as potentially useful for gene therapy in cancers deleted or altered in their expression of that gene. Frzb-1 maps to chromosome 2q31-33 and loss of one copy of the 2q31-33 and loss of one copy of the 2q arm has been observed with high incidence in lung carcinomas, colo-rectal carcinomas, and neuroblastomas, which has lead to the proposal that the 2q arm carries a tumor suppressor gene. We expect frzb to be a tumor suppressor gene, and thus to be useful in tumor suppression applications.

A number of applications for cerberus and frzb-1 are suggested from their pharmacological (biological activity) properties.

For example, the cerberus and frzb-1 cDNAs should be useful as a diagnostic tool (such as through use of antibodies in assays for proteins in cell lines or use of oligonucleotides as primers in a PCR test to amplify those with sequence similarities to the oligonucleotide primer, and to determine how much of the novel protein is present).

Cerberus, of course, might act upon its target cells via its own receptor. Cerberus, therefore, provides the key to isolate this receptor. Since many receptors mutate to cellular oncogenes, the cerberus receptor should prove useful as a diagnostic probe for certain tumor types. Thus, when one views cerberus as ligand in complexes, then complexes in accordance with the invention include antibody bound to cerberus, antibody bound to peptides derived from cerberus, cerberus bound to its receptor, or peptides derived from cerberus bound to its receptor or other factors. Mutant forms of cerberus, which are either more potent agonists or antagonists, are believed to be clinically useful. Such complexes of cerberus and its binding protein partners will find uses in a number of applications.

Practice of this invention includes use of an oligonucleotide construct comprising a sequence coding for cerberus or frzb-1 and for a promoter sequence operatively linked in a mammalian or a viral expression vector. Expression and cloning vectors contain a nucleotide sequence that enables the vector to replicate in one or more selected host cells. Generally, in cloning vectors this sequence is one that enables the vector to replicate independently of the host chromosomes, and includes origins of replication or autonomously replicating sequences. The well-known plasmid pBR322 is suitable for most gram negative bacteria, the $2\mu$ plasmid origin for yeast and various viral origins (SV40, polyoma, adenovirus, VSV or BPV) are useful for cloning vectors in mammalian cells.

Expression and cloning vectors should contain a selection gene, also termed a selectable marker. Typically, this is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies.

Examples of suitable selectable markers for mammalian cells are dihydrofolate reductase (DHFR) or thymidine kinase. Such markers enable the identification of cells which were competent to take up the cerberus nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed. Amplification is the process by which genes in greater demand for the production of a protein critical for growth are reiterated in tandem within the chromosomes of successive generations of recombinant cells. Increased quantities of cerberus or frzb-1 can therefor be synthesized from the amplified DNA.

For example, cells transformed with the DHFR selection gene are first identified by culturing all of the transformants in a culture medium which contains methotrexate (Mtx), a competitive antagonist of DHFR. An appropriate host cell in this case is the Chinese hamster ovary (CHO) cell line deficient in DHFR activity, prepared and propagated as described by Urlaub and Chasin, *Proc. Nat. Acac. Sci.*, 77, 4216 (1980). The transformed cells then are exposed to increased levels of Mtx. This leads to the synthesis of multiple copies of the DHFR gene and, concomitantly, multiple copies of other DNA comprising the expression vectors, such as the DNA encoding cerberus or frzb-1. Alternatively, host cells transformed by an expression vector comprising DNA sequences encoding cerberus or frzb-1 and aminoglycoside 3' phosphotransferase (APH) protein can be selected by cell growth in medium containing an aminoglycosidic antibiotic such as kanamycin or neomycin or G418. Because eukaryotic cells do not normally express an endogenous APH activity, genes encoding APH protein, commonly referred to as neo resistant genes, may be used as dominant selectable markers in a wide range of eukaryotic host cells, by which cells transformed by the vector can readily be identified.

Expression vectors, unlike cloning vectors, should contain a promoter which is recognized by the host organism and is operably linked to the cerberus nucleic acid. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters can be operably linked to cerberus encoding DNA by removing them from their gene of origin by restriction enzyme digestion, followed by insertion 5' to the start codon for cerberus or frzb-1.

Nucleic acid is operably linked when it is placed into a functional relationship with another nucleic acid sequence. For example, DNA for a presequence or secretory leader is operably linked to DNA for a polypeptide if it is expressed as a preprotein which participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous and, in the case of a secretory leader, contiguous and in reading phase. Linking is accomplished by ligation at convenient restriction sites. If such sites do not exit then synthetic oligonucleotide adapters or linkers are used in accord with conventional practice.

Transcription of the protein-encoding DNA in mammalian host cells is controlled by promoters obtained from the genomes of viruses such as polyoma, cytomegalovirus, adenovirus, retroviruses, hepatitis-B virus, and most preferably Simian Virus 40 (SV40), or from heterologous mammalian promoters, e.g. the actin promoter. Of course, promoters from the host cell or related species also are useful herein.

Cerberus and frzb-1 are clearly useful as a component of culture media for use in culturing cells, such as endodermal, cardiac, and nerve cells, in vitro. We believe cerberus and frzb-1 will find uses as agents for enhancing the survival or inducing the growth of liver, pancreas, heart, and nerve cells, such as in tissue replacement therapy.

The final cDNA isolated containing a signal sequence results in a peptide designated Paraxial Protocadherin (PAPC). The cDNA for PAPC is a divergent member of the cadherin multigene family. PAPC is most related to protocadherin 43 reported by Sano et al., *The EMBO J.*, 12, pp. 2249–2256, 1993. As shown in SEQ ID NO:5, the PAPC gene encodes a transmembrane protein of 896 amino acids, of which 187 are part of an intracellular domain. PAPC is a cell adhesion molecule, and microinjection of PAPC mRNA constructs into Xenopus embryos suggest that PAPC acts in mesoderm differentiation. The nucleotide sequence encoding Xenopus PAPC is provided in SEQ ID NO:6.

Therapeutic formulations of the novel proteins may be prepared for storage by mixing the polypeptides having the desired degree of purity with optional physiologically acceptable carriers, excipients or stabilizers, in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin or immunoglobulins. Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Polyclonal antibodies to the novel proteins generally are raised in animals by multiple subcutaneous (sc) or intraperitoneal (ip) injections of cerberus or frzb-1 and an adjuvant. It may be useful to conjugate these proteins or a fragment containing the target amino acid sequence to a protein which is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$.

Animals can be immunized against the immunogenic conjugates or derivatives by combining 1 mg or 1 μg of conjugate (for rabbits or mice, respectively) with 3 volumes of Freund's complete adjuvant and injecting the solution intradermally in multiple sites. One month later the animals are boosted with ⅕ to ¹⁄₁₀ the original amount of conjugate in Fruend's complete adjuvant by subcutaneous injection at multiple sites. Seven to 14 days later animals are bled and the serum is assayed for anti-cerberus titer. Animals are boosted until the titer plateaus. Preferably, the animal is boosted with the conjugate of the same cerberus or frzb-1 polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering spleen cells from immunized animals and immortalizing the cells in conventional fashion, e.g. by fusion with myeloma cells or by EB virus transformation and screening for clones expressing the desired antibody.

Antibodies are useful in diagnostic assays for cerberus, frzb-1, or PAPC or their antibodies and to identify family members. In one embodiment of a receptor binding assay, an antibody composition which binds to all of a selected plurality of members of the cerberus family is immobilized on an insoluble matrix, the test sample is contacted with the immobilized antibody composition in order to adsorb all cerberus family members, and then the immobilized family members are contacted with a plurality of antibodies specific for each member, each of the antibodies being individually identifiable as specific for a predetermined family member, as by unique labels such as discrete fluorophores or the like. By determining the presence and/or amount of each unique label, the relative proportion and amount of each family member can be determined.

The antibodies also are useful for the affinity purification of the novel proteins from recombinant cell culture or natural sources. Antibodies that do not detectably cross-react with other growth factors can be used to purify the proteins free from these other family members.

EXAMPLE 1

Frzb-1 Antagonizes Xwnt-8 Non-Cell Autonomously

To test whether frzb-1 can antagonize secondary axes caused by Xwnt-8 after secretion by injected cells, an experimental design was used. Thus, frzb-1 mRNA was injected into each of the four animal blastomeres of eight-cell embryos, and subsequently, a single injection of Xwnt-8 mRNA was given to a vegetal-ventral blastomere at the 16–32 cell stage. In two independent experiments, we found that injection of frzb-1 alone (n=13) caused mild dorsalization with enlargement of the cement gland in all embryos and that injection of Xwnt-8 alone (n=53) lead to induction of complete secondary axes in 67% of the embryos. However, injection of frzb-1 into animal caps abolished the formation of complete axes induced by Xwnt-8 (n=27), leaving only a residual 14% of embryos with very weak secondary axes. The double-injected embryos retained the enlarged cement gland phenotype caused by injection of frzb-1 mRNA alone. Because both mRNAs encode secreted proteins and were microinjected into different cells, we conclude that the antagonistic effects of frzb-1 and Xwnt-8 took place in the extracellular space after these proteins were secreted.

EXAMPLE 2

Membrane-Anchored Wnt-1 Confers Frzb-1 Binding

To investigate a possible interaction between frzb-1 and Wnts, the first step was to insert an HA epitope tag into a Xenopus frzb-1 construct driven by the CMV (cytomegalovirus) promoter. Frzb1-HA was tested in mRNA microinjection assays in Xenopus embryos and found to be biologically active. Conditioned medium from transiently transfected cells contained up to 10 µg/ml of Frzb1-HA (quantitated on Western blots using an HA-tagged protein standard).

Transient transfection of 293 cells has been instrumental in demonstrating interactions between wingless and frizzled proteins. We therefore took advantage of constructs in which Wnt-1 was fused at the amino terminus of cD8, generating a transmembrane protein containing biologically active Wnt-1 exposed to the extracellular compartment. A Wnt1cD8 cDNA construct (a generous gift of Dr. H. Varmus, NIH) was subcloned into the pcDNA (Invitrogen) vector and transfected into 293 cells. After incubation with Frzb1-HA-conditioned medium (overnight at 37° C.), intensely labeled cells were observed by immunofluorescence. As a negative control, a construct containing 120 amino acids of Xenopus chordin, an unrelated secreted protein was used. Transfection of this construct produced background binding of Frzb1-HA to the extracellular matrix, both uniform and punctate. Cotransfection of Wnt1cD8 with pcDNA-LacZ showed that transfected cells stained positively for Frzb1-HA and LacZ. Since Wnt1cD8 contains the entire cD8 molecule, a cD8 cDNA was used as an additional negative control. After transfection with LacZ and full-length CE8, Frzb1-HA failed to bind to the transfected cells. Although most of our experiments were carried out at 37° C., Frzb1-HA-conditioned medium also stained Wnt1cD8-transfected cells after incubation at 4° C. for 2 hours.

Attempts to biochemically quantitate the binding of Frzb-1 to Wnt1cD8-transfected cells were unsuccessful due to high background binding to control cultures, presumably due to binding to the extracellular matrix. Thus, we were unable to estimate a $K_D$ for the affinity of the Frzb-1/Wnt-1 interaction. However, when serial dilutions of conditioned medium containing Frzb1-HA were performed (ranging from $2.5 \times 10^{-7}$ to $1.25 \times 10^{-10}$ M), staining of Wnt1cD8-transfected cells was found at all concentrations.

Although we have been unable to provide biochemical evidence for direct binding between Wnts and frzb-1, this cell biological assay indicates that Frzb1-HA can bind, directly or indirectly, to Wnt-1 on the cell membrane in the $10^{-10}$ M range.

It is to be understood that while the invention has been described above in conjunction with preferred specific embodiments, the description and examples are intended to illustrate and not limit the scope of the invention, which is defined by the scope of the appended claims.

It is claimed:

1. A substantially pure protein comprising either the amino acid sequence of SEQ ID NO:1 or a fragment thereof, wherein said fragment has neurotrophic, growth or differentiation factor activity in Xenopus embryos, and wherein said protein does not dorsalize Xenopus mesoderm.

2. A composition comprising a substantially pure protein and a physiologically acceptable carrier with which the protein is admixed, wherein said protein comprises either the amino acid sequence of SEQ ID NO:1 or a fragment thereof, wherein said fragment has neurotrophic, growth or differentiation factor activity in Xenopus embryos.

3. The composition of claim 2, wherein said protein has nine cysteine residues.

4. The composition of claim 2, wherein said protein does not dorsalize Xenopus mesoderm.

5. The composition of claim 3, wherein said protein has multiple glycosylation sites.

6. An article of manufacture comprising a protein that has been derivatized so as to be immobilized on a solid support, wherein said protein comprises either the amino acid sequence of SEQ ID NO:1 or a fragment thereof, wherein said fragment has neurotrophic, growth or differentiation factor activity in Xenopus embryos.

7. The article of claim 6, wherein said protein has nine cysteine residues.

8. The article of claim 6, wherein said protein does not dorsalize Xenopus mesoderm.

9. The article of claim 6, wherein said protein has multiple glycosylation sites.

10. The article of claim 6, wherein said protein includes a label.

* * * * *